(12) United States Patent
Bakale et al.

(10) Patent No.: US 9,913,827 B2
(45) Date of Patent: *Mar. 13, 2018

(54) BENDAMUSTINE DERIVATIVES AND METHODS OF USING SAME

(71) Applicant: IGNYTA, INC., San Diego, CA (US)

(72) Inventors: Roger P. Bakale, Malvern, PA (US); Peter D. Brown, West Chester, PA (US); Jian Chen, West Chester, PA (US); Anthony S. Drager, Thorndale, PA (US); Rachel Y. LaBell, Coatesville, PA (US); Robert E. McKean, Chester Springs, PA (US); Piyush R. Patel, Wallingford, PA (US); Renee C. Roemmele, Maple Glen, PA (US)

(73) Assignee: IGNYTA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/456,439

(22) Filed: Mar. 10, 2017

(65) Prior Publication Data

US 2017/0182008 A1 Jun. 29, 2017

Related U.S. Application Data

(63) Continuation of application No. 15/184,968, filed on Jun. 16, 2016, now Pat. No. 9,630,926, which is a continuation of application No. 14/868,278, filed on Sep. 28, 2015, now abandoned, which is a continuation of application No. 14/699,965, filed on Apr. 29, 2015, now Pat. No. 9,150,517, which is a continuation of application No. PCT/US2013/069550, filed on Nov. 12, 2013.

(60) Provisional application No. 61/725,213, filed on Nov. 12, 2012, provisional application No. 61/776,951, filed on Mar. 12, 2013.

(51) Int. Cl.
| | |
|---|---|
| A61K 31/4184 | (2006.01) |
| C07D 235/16 | (2006.01) |
| A61K 47/42 | (2017.01) |
| A61K 9/14 | (2006.01) |

(52) U.S. Cl.
CPC ............ *A61K 31/4184* (2013.01); *A61K 9/14* (2013.01); *A61K 47/42* (2013.01); *C07D 235/16* (2013.01)

(58) Field of Classification Search
CPC ......................... A61K 31/4184; C07D 235/16
See application file for complete search history.

(56) References Cited

U.S. PATENT DOCUMENTS

| 5,681,964 A | 10/1997 | Ashton et al. |
|---|---|---|
| 7,758,891 B2 | 7/2010 | Desai et al. |
| RE41,884 E | 10/2010 | De Garavilla et al. |
| 7,820,788 B2 | 10/2010 | Desai et al. |
| 7,923,536 B2 | 4/2011 | Desai et al. |
| 8,034,375 B2 | 10/2011 | Desai et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,006 B2 | 1/2013 | Drager et al. |
| 8,436,190 B2 | 5/2013 | Brittain et al. |
| 8,445,524 B2 | 5/2013 | Courvoisier et al. |
| 8,461,350 B2 | 6/2013 | Brittain et al. |
| 8,481,751 B2 | 7/2013 | Groh et al. |
| 8,609,863 B2 | 12/2013 | Brittain et al. |
| 8,669,279 B2 | 3/2014 | Cooper et al. |
| 8,791,270 B2 | 7/2014 | Brittain et al. |
| 8,809,549 B2 | 8/2014 | Schickaneder et al. |
| 8,853,260 B2 | 10/2014 | Desai et al. |
| 8,883,836 B2 | 11/2014 | Cooper et al. |
| 8,895,756 B2 | 11/2014 | Brittain et al. |
| 9,149,464 B2 | 10/2015 | Bakale et al. |
| 9,150,517 B2 | 10/2015 | Bakale et al. |
| 9,452,988 B2 * | 9/2016 | Bakale ................. C07D 235/16 |
| 2006/0165987 A1 | 7/2006 | Hildgen et al. |
| 2010/0111984 A1 | 5/2010 | D'Souza |
| 2012/0165543 A1 | 6/2012 | Groh et al. |
| 2014/0045950 A1 | 2/2014 | Lacko et al. |
| 2014/0121383 A1 | 5/2014 | Mishra et al. |
| 2015/0274675 A1 | 10/2015 | Bakale et al. |
| 2016/0016912 A1 | 1/2016 | Bakale et al. |

FOREIGN PATENT DOCUMENTS

| CN | 101966158 | 2/2011 |
|---|---|---|
| CN | 102281871 A | 12/2011 |
| EP | 2 468 716 | 6/2012 |
| JP | 2004-518776 | 6/2004 |
| JP | 2008-526991 | 7/2008 |
| JP | 2011-504937 | 2/2011 |
| JP | 2012-503666 | 2/2012 |
| JP | 2012-131790 | 7/2012 |
| WO | WO-02/43663 | 6/2002 |
| WO | WO-2006/076620 | 7/2006 |

(Continued)

OTHER PUBLICATIONS

A. Nayak and A. Jain. In Vitro and in Vivo Study of Poly(ethylene glycol) Conjugated Ibuprofen to Extend the Duration of Action. Sci Pharm. Apr.-Jun. 2011;79(2):359-73.
ABRAXANE Package Insert, Revised Dec. 2014, 24 pages.
Dubbelman, A-C et al., "Metabolite Profiling of Bendamustine in Urine of Cancer Patients after Administration of [14C]Bendamustine", Drug Metabolism and Disposition, vol. 40, No. 7, (2012), pp. 1297-1307.
English Translation of CN 101966158 (Hou et al), 2011.
Hagemeister et al., Onco Targets and Therapy, 2009, 2 pp. 269-279.
International Preliminary Report on Patentability on International Application No. PCT/EP2013/062347, dated Dec. 31, 2014, 9 pages.
International Preliminary Report on Patentability on International Application No. PCT/US2013/069550, dated May 21, 2015, 6 pages.

(Continued)

*Primary Examiner* — Laura L Stockton
(74) *Attorney, Agent, or Firm* — Foley & Lardner LLP

(57) ABSTRACT

The present invention is directed to bendamustine esters and bendamustine amides and their use for the treatment of cancer.

20 Claims, 24 Drawing Sheets

(56) References Cited

FOREIGN PATENT DOCUMENTS

| WO | WO-2009/070761 | 6/2009 |
| WO | WO 2010/036702 | 4/2010 |
| WO | WO-2010/036702 | 4/2010 |
| WO | WO-2010/042568 A1 | 4/2010 |
| WO | WO-2010/063493 A1 | 6/2010 |
| WO | WO-2011/151087 | 12/2011 |
| WO | WO-2011/151087 A1 | 12/2011 |
| WO | WO 2011/151807 | 12/2011 |
| WO | WO-2012/059935 | 5/2012 |
| WO | WO-2012/154861 A2 | 11/2012 |
| WO | WO-2012/158776 | 11/2012 |
| WO | WO-2013/189847 | 12/2013 |

OTHER PUBLICATIONS

International Search Report and Written Opinion on International Application No. PCT/EP2013/062347, dated Sep. 10, 2013, 14 pages.

International Search Report and Written Opinion on International Application No. PCT/US2013/069550, dated Jan. 2, 2014, 8 pages.

Ji, Tzeng, et al. Pharmacokinetics of ketorolac pentyl ester, a novel ester derivative of ketorolac, in rabbits. Kaohsiung J Med Sci. Aug. 2005;21(8):365-70.

Rautio et al., Prodrugs: design and clinical application. Nature Reviews Drug Discovery, Mar. 2008, 7(3), pp. 255-270.

Scutaru, Ana Maria et al., "Bivalent bendamustine and melphalan derivatives as anticancer agents", European Journal of Medicinal Chemistry, vol. 46, No. 5, (2011), pp. 1604-1615.

Scutaru, Ana Maria et al., "Optimization of the N-Lost Drugs Melphalan and Bendamustine: Synthesis and Cytotoxicity of a New Set of Dendrimer-Drug Conjugates as Tumor Therapeutic Agents", Bioconjugate Chemistry, vol. 21, No. 10, (2010), pp. 1728-1743.

TREANDA package insert, Revised Mar. 2015, 7 pages.

Calver et al., "Physicochemical and pharmacokinetic parameters of seven lipophilic chlorambucil esters designed for brain penetration", Cancer Chemotherapy and Pharmacology, 1990, 25(5), pp. 311-319.

* cited by examiner

BENDAMUSTINE DERIVATIVES AND METHODS OF USING SAME

CROSS-REFERENCE TO RELATED APPLICATIONS

This application is a continuation of U.S. application Ser. No. 15/184,968, filed on Jun. 16, 2016, which is a continuation of U.S. application Ser. No. 14/868,278, filed on Sep. 28, 2015, which is a continuation of U.S. application Ser. No. 14/699,965, filed on Apr. 29, 2015, which is a continuation of PCT Application No. PCT/US2013/069550, filed on Nov. 12, 2013, entitled "Bendamustine Derivatives and Methods of Using Same," which claims the benefit of U.S. Provisional Application No. 61/725,213, filed Nov. 12, 2012, and U.S. Provisional Application No. 61/776,951, filed Mar. 12, 2013, the entireties of which are incorporated by reference herein.

TECHNICAL FIELD

The present invention is directed to esters and amides of bendamustine for use in treating cancer.

BACKGROUND

Bendamustine, 4-[5-[bis(2-chloroethyl)amino]-1-methyl-benzimidazol-2-yl]butanoic acid:

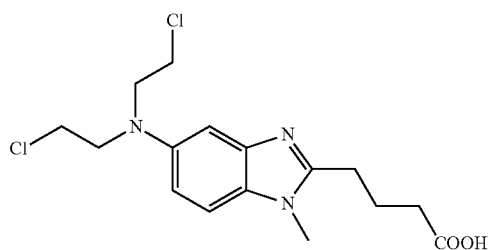 [SMILES: Cn1c(CCCC(=O)O)nc2cc(N(CCCl)CCCl)ccc21]

is marketed as the hydrochloride salt under the trade names RIBOMUSTIN and TREANDA and is a compound that has been used successfully for the treatment of blood cancers such as chronic lymphocytic leukemia, Hodgkin's disease, non-Hodgkin's lymphoma, and multiple myeloma. These products are administered as intravenous infusions.

Use of bendamustine for the treatment of solid tumors is limited, however, by the compound's chemical instability in aqueous environment. Indeed, bendamustine has been reported as having a half-life of only about 6-10 minutes in vivo. As a result, circulating levels of bendamustine are not sustained for a long enough time for bendamustine to reach tumors outside of the circulatory system. Methods for increasing the circulation time of bendamustine are needed.

SUMMARY

The present invention is directed to compounds of formula I:

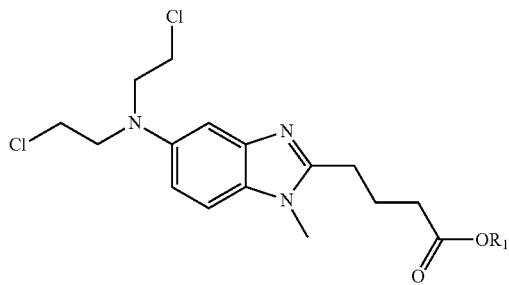

wherein $R_1$ is $C_6$-$C_{24}$alkyl or polyethylene glycol; or pharmaceutically acceptable salt forms thereof. Methods of using compounds of formula I for the treatment of solid and non-solid cancer tumors are also described.

The invention is also directed to the use of compounds of formula IA:

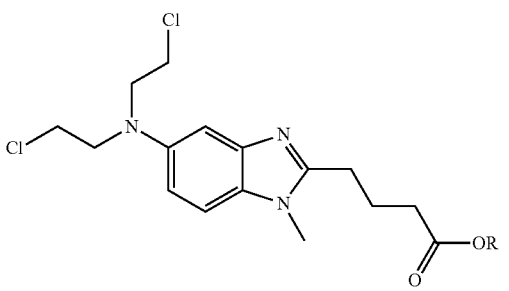

wherein R is $C_1$-$C_{24}$alkyl or polyethylene glycol; or pharmaceutically acceptable salt forms thereof for the treatment of solid and non-solid cancer tumors.

The invention is further directed to compounds of formula II:

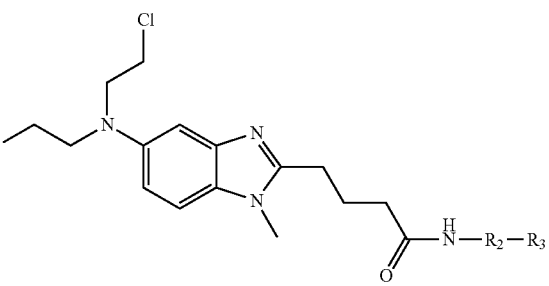

wherein $R_2$ is $C_1$-$C_{24}$alkylene; and $R_3$ is —COOC$_{1-3}$alkyl; or $R_2$-$R_3$ is $C_1$-$C_{24}$alkyl; or pharmaceutically acceptable salt forms thereof. Methods of using compounds of formula II for the treatment of solid and non-solid cancer tumors.

Nanoparticles including compounds of Formula I or IA, as well as lyophilized compositions comprising those nanoparticles, are also within the scope of the invention.

DETAILED DESCRIPTION OF ILLUSTRATIVE EMBODIMENTS

Figure 1:
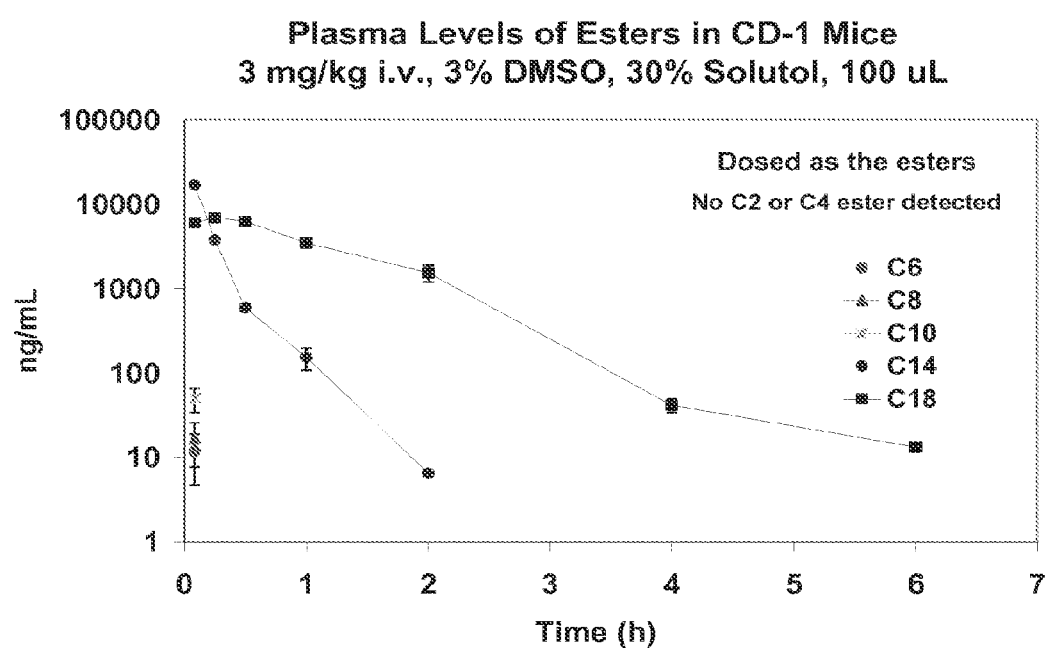
FIG. 1 depicts plasma levels of certain embodiments of the invention in CD-1 mice, dosing at 3 mg/kg i.v. in 3% DMSO, 30% Solutol, 100 µL.

It has been discovered that converting the carboxylic acid moiety of bendamustine to a $C_1$-$C_{24}$alkyl ester group, a polyethylene glycol ester group, or a $C_1$-$C_{24}$alkyl amide group results in compounds that provide longer circulating times for bendamustine. While not wishing to be bound to any particular theory, it is presumed that the ester or amide moiety reduces the solubility of the bendamustine molecule, resulting in a protective effect against the aqueous environment. Over time, the ester or amide moiety is hydrolyzed to reveal the carboxylic acid moiety of the active bendamustine molecule. The overall result is that bendamustine is generated over time.

By varying the number of carbons in the ester/amide moiety, the lipophilicity of the resulting bendamustine derivative can be modified. Increasing lipophilicity has been correlated to increased stability of the ester/amide and longer circulating times of bendamustine.

Within the scope of the invention are compounds of formula IA:

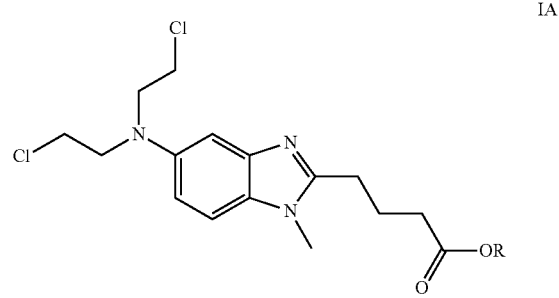

wherein R is $C_1$-$C_{24}$alkyl or polyethylene glycol; or a pharmaceutically acceptable salt form thereof. Compounds of formula IA are useful for the treatment of solid or non-solid cancer tumors in patients.

Compounds of the invention can be formulated into pharmaceutical compositions comprising the compound of formula IA, or a pharmaceutically acceptable salt form thereof, and a pharmaceutically acceptable carrier or diluent. In preferred pharmaceutical compositions of the invention, R is $C_{10}$-$C_{24}$alkyl. Preferably, R is $C_{10}$alkyl. Also preferred is where R is $C_{12}$alkyl. Other preferred embodiments include those where R is $C_{14}$alkyl. Compositions where R is $C_{16}$alkyl are also preferred.

Other embodiments of the invention include nanoparticles comprising a compound of formula IA.

Also within the scope of the invention are methods of treating solid or non-solid cancer tumors in patients comprising administering to the patient a compound of formula IA. Preferred solid or non-solid tumors include chronic lymphocytic leukemia, Hodgkin's disease, indolent non-Hodgkin's lymphoma (T-cell lymphoma, B-cell lymphoma), aggressive non-Hodgkin's lymphoma, multiple myeloma, acute lymphocytic leukemia, breast cancer or lung cancer (small cell lung cancer (SCLC) and non-small cell lung cancer (NSCLC), for example). Other solid and non-solid cancer tumors are also envisioned as being treatable with compounds and compositions of the invention, such as for example, sarcoma, bladder cancer, cervical cancer, testicular cancer, melanoma, glioblastoma, colon cancer, head and neck cancer, ovarian cancer, and prostate cancer. Other solid and non-solid cancer tumors are also envisioned as being treatable with compounds of the invention, for example, breast cancer, pancreatic cancer, and gastric cancer.

Preferred compounds of the invention are those of formula I:

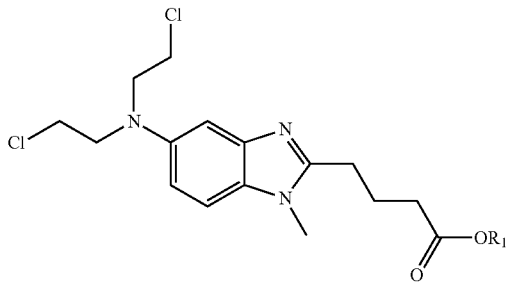

wherein $R_1$ is $C_6$-$C_{24}$alkyl or polyethylene glycol; or a pharmaceutically acceptable salt form thereof. Compounds of formula I are useful for the treatment of solid or non-solid cancer tumors in patients.

In preferred embodiments, $R_1$ is $C_8$-$C_{24}$alkyl. In other embodiments, $R_1$ is $C_{10}$-$C_{24}$alkyl. In yet other embodiments, $R_1$ is $C_{12}$-$C_{24}$alkyl. In still other embodiments, $R_1$ is $C_{14}$-$C_{24}$alkyl. Also preferred are those compounds of formula I wherein $R_1$ is $C_{16}$-$C_{24}$alkyl. In other embodiments, $R_1$ is $C_{18}$-$C_{24}$alkyl.

In other embodiments, $R_1$ is $C_{10}$alkyl. In yet other embodiments, $R_1$ is $C_{12}$alkyl. In still other embodiments, $R_1$ is $C_{14}$alkyl. In other embodiments, $R_1$ is $C_{16}$alkyl.

Also within the scope of the invention are pharmaceutical compositions comprising a compound of formula I and a pharmaceutically acceptable carrier or diluent.

Other embodiments of the invention include nanoparticles comprising a compound of formula I.

Also within the scope of the invention are methods of treating cancer comprising administering to a patient a compound of formula I. A number of cancers, including those that involve solid tumors as well as those that do not involve solid tumors may be amenable to such treatment. These cancers include chronic lymphocytic leukemia, Hodgkin's disease, indolent non-Hodgkin's lymphoma (T-cell lymphoma, B-cell lymphoma), aggressive non-Hodgkin's lymphoma, multiple myeloma, acute lymphocytic leukemia, breast cancer or lung cancer (small cell lung cancer (SCLC) and non-small cell lung cancer (NSCLC), for example). Additional cancers that are also envisioned as being treatable with compounds and compositions of the invention are those characterized by the presence of solid tumors, include sarcoma, bladder cancer, cervical cancer, testicular cancer, melanoma, glioblastoma, colon cancer, head and neck cancer, ovarian cancer, and prostate cancer. Other solid and non-solid cancer tumors are also envisioned as being treatable with compounds of the invention, for example, breast cancer, pancreatic cancer, and gastric cancer.

Particularly preferred compounds of the invention include:

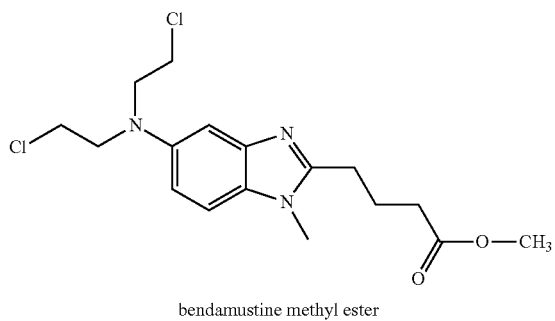

bendamustine methyl ester

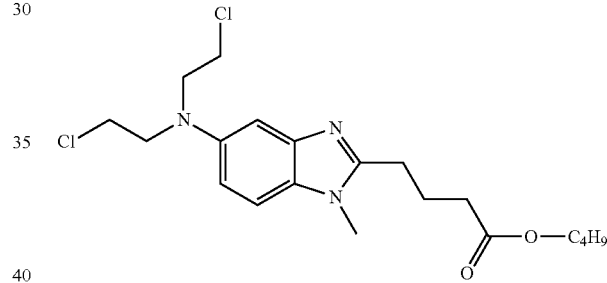

bendamustine $C_4$ ester

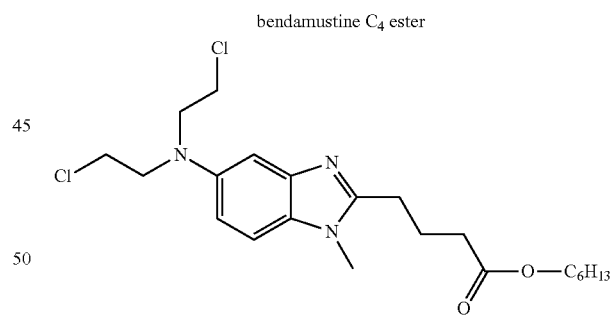

bendamustine $C_6$ ester

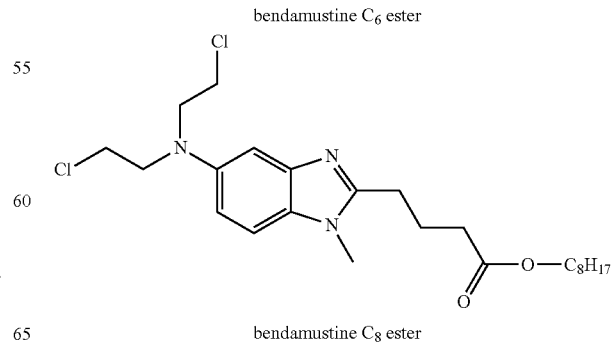

bendamustine $C_8$ ester

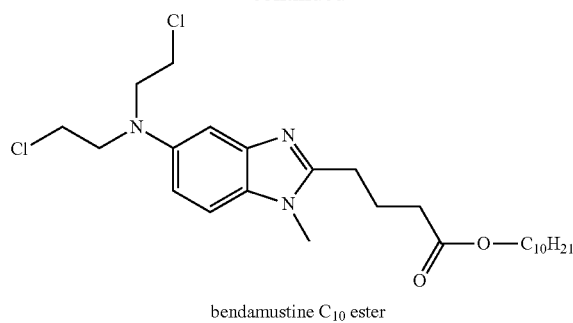

bendamustine C$_{10}$ ester

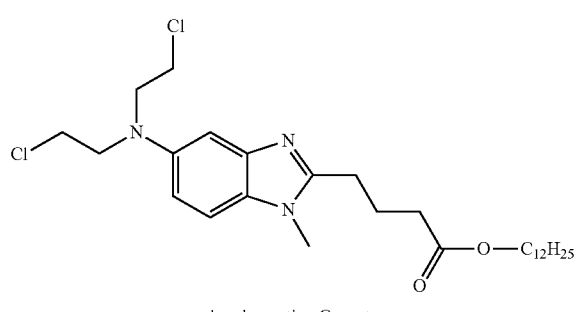

bendamustine C$_{12}$ ester

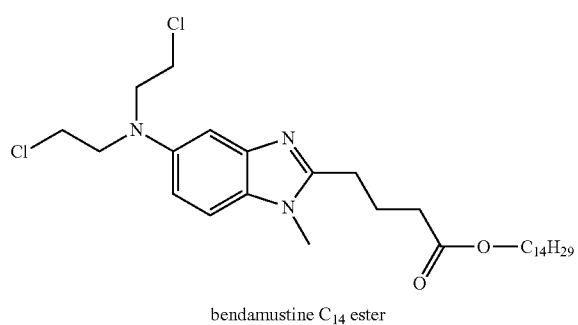

bendamustine C$_{14}$ ester

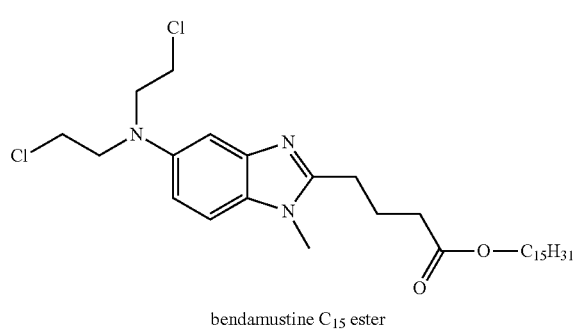

bendamustine C$_{15}$ ester

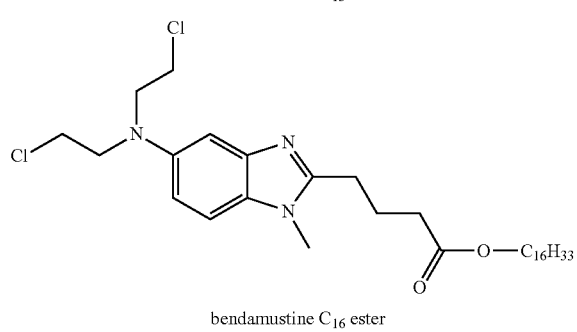

bendamustine C$_{16}$ ester

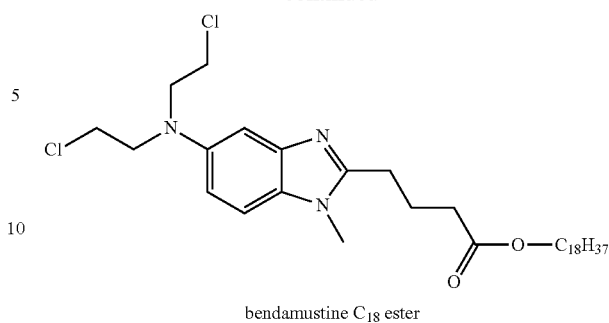

bendamustine C$_{18}$ ester

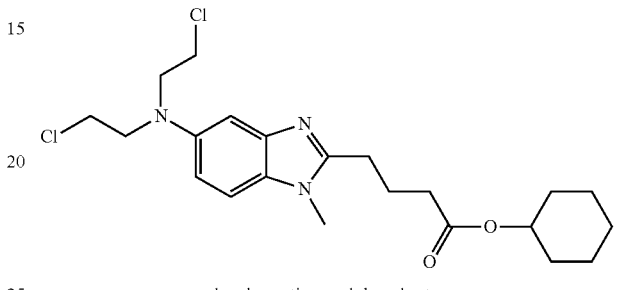

bendamustine cyclohexyl ester

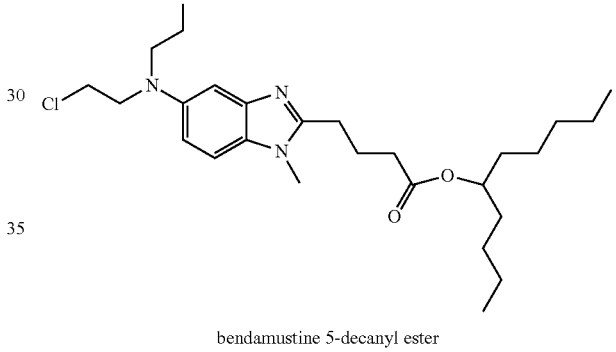

bendamustine 5-decanyl ester

Also within the scope of the invention are compounds of formula II:

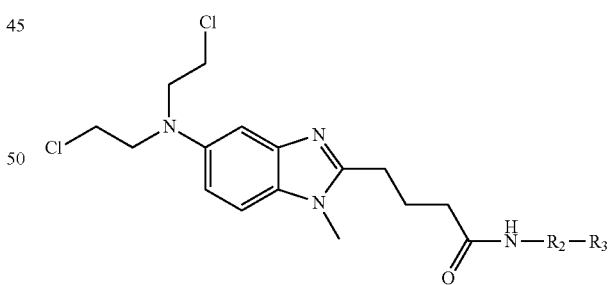

wherein $R_2$ is $C_1$-$C_{24}$alkylene; and $R_3$ is —COO$C_{1-3}$alkyl; or $R_2$-$R_3$ is $C_1$-$C_{24}$alkyl; or a pharmaceutically acceptable salt form thereof. Compounds of formula II are useful for the treatment of solid or non-solid cancer tumors in patients.

In preferred embodiments of compounds of formula II, $R_2$-$R_3$ is $C_8$-$C_{24}$alkyl. In other embodiments, $R_2$-$R_3$ is $C_{10}$-$C_{24}$alkyl. In still other embodiments, $R_2$-$R_3$ is $C_{12}$-$C_{24}$alkyl. In yet other embodiments, $R_2$-$R_3$ is $C_{14}$-$C_{24}$alkyl. Also preferred is when $R_2$-$R_3$ is $C_{16}$-$C_{24}$alkyl. In other embodiments, $R_2$-$R_3$ is $C_{18}$-$C_{24}$alkyl.

Preferably, for compounds of formula II, $R_2$-$R_3$ is $C_{10}$alkyl. Also preferred is when $R_2$-$R_3$ is $C_{12}$alkyl. In other embodiments, $R_2$-$R_3$ is $C_{14}$alkyl. In yet other embodiments, $R_2$-$R_3$ is $C_{16}$alkyl.

In other embodiments, $R_2$ is $C_2$alkylene and $R_3$ is —COOCH$_3$.

Preferred compounds of formula II include:

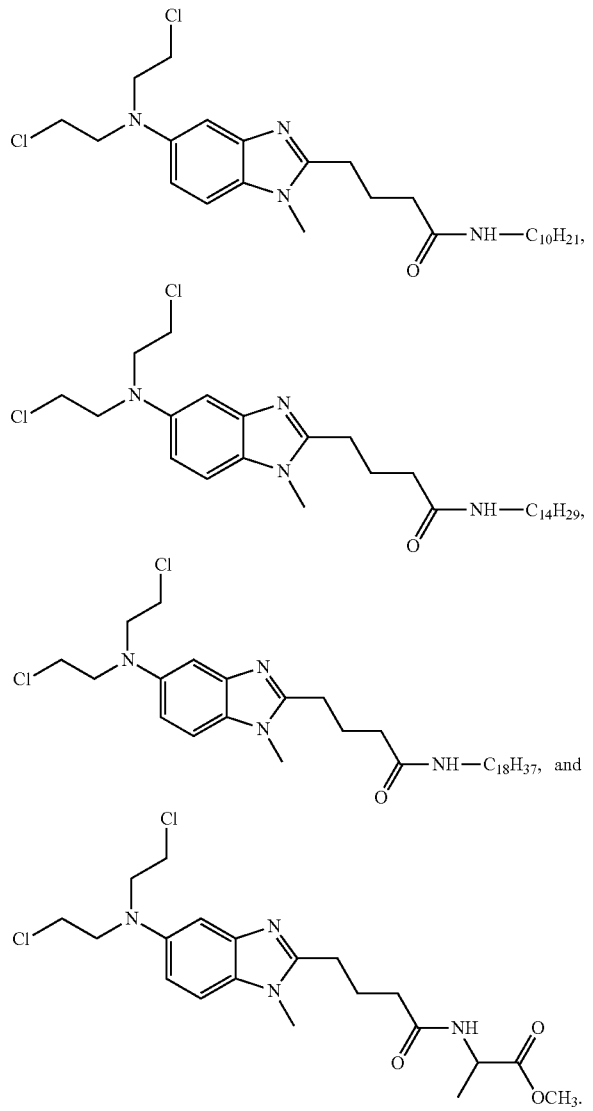

Also within the scope of the invention are pharmaceutical compositions comprising a compound of formula II and a pharmaceutically acceptable carrier or diluent.

Other embodiments of the invention include nanoparticles comprising a compound of formula II.

In one embodiment of the invention, the compounds and compositions of the invention are used to treat patients who are resistant to one or more chemotherapeutic agents, such as, for example, alkylating agents. Exemplary alkylating agents to which patients may be resistant include: nitrogen mustards; ethylenimines; alkylsulfonates; triazenes; piperazines; and nitrosureas. More specific examples of the various types of chemotherapeutic agents to which patients can become resistant are listed below. Patients resistant to one or more of these agents would benefit by treatment with the compounds and compositions of the invention.

Nitrogen Mustards

Mechlorethamine, marketed under the trade name Mustargen®, is given by injection to treat Hodgkin's disease and non-Hodgkin's lymphoma, and as a palliative therapy for breast and lung cancers, and given as a topical treatment for skin lesions of mycosis fungoides (cutaneous T-cell lymphoma).

Ifosfamide, sold under the trade name Ifex®, is used to treat both Hodgkin's and non-Hodgkin's lymphoma, as well as recurrent testicular cancer and germ cell tumors, sarcomas, lung cancer, bladder cancer, head and neck cancer, and cervical cancer.

Melphalan is a chemotherapy drug sold under the brand name Alkeran®, and is also referred to as L-PAM or phenylalanine mustard. It is used to treat multiple myeloma, ovarian cancer, neuroblastoma, rhabdomyosarcoma, and breast cancer.

Chlorambucil is sold by the trade name Leukeran®, and is most widely used to treat chronic lymphocytic leukemia, malignant lymphomas including lymphosarcoma, giant follicular lymphoma, and Hodgkin's disease. It has also been successfully used to treat non-Hodgkin's lymphoma, breast, ovarian and testicular cancer, Waldenstrom's macroglobulinemia, thrombocythemia, and choriocarcinoma.

Cyclophosphamide is marketed as Cytoxan® or Neosar®, and is used to treat Hodgkin's and non-Hodgkin's lymphoma, Burkitt's lymphoma, chronic lymphocytic leukemia, chronic myelocytic leukemia, acute myelocytic leukemia, acute lymphocytic leukemia, t-cell lymphoma, multiple myeloma, neuroblastoma, retinoblastoma, rhabdomyosarcoma, Ewing's sarcoma; breast, testicular, endometrial, ovarian, and lung cancers.

Nitrosoureas

Streptozocin is sold under the trade name Zanosar®, and is used to treat islet cell pancreatic cancer.

Carmustine is also known as BiCNU® or BCNU, and is used for some kinds of brain tumors, glioblastoma, brainstem glioma, medulloblastoma, astrocytoma, ependymoma, and metastatic brain tumors. It is also used in treatment for multiple myeloma, Hodgkin's disease, non-Hodgkin's lymphoma, melanoma, lung cancer, and colon cancer.

Lomustine, also known as CCNU or CeeNU®, is used to treat primary and metastatic brain tumors, Hodgkin's disease and non-Hodgkin's lymphoma, and has also been used for melanoma, lung, and colon cancer.

Alkyl Sulfonates

Busulfan, sold under trade names Busulfex® and Myleran®, is used to treat chronic myelogenous leukemia.

Triazines

Dacarbazine is sold under the trade name DTIC-Dome® and is used to treat metastatic malignant melanoma, Hodgkin's disease, soft tissue sarcomas, neuroblastoma, fibrosarcomas, rhabdomyosarcoma, islet cell carcinoma, and medullary thyroid carcinoma.

Temozolomide is sold under the trade name Temodar®, and is used to treat the specific types of brain tumors anaplastic astrocytoma and glioblastoma multiforme.

Ethylenimines

Thiotepa, known under the trade name Thioplex®, is an alkylating agent used to treat breast cancer, ovarian cancer, Hodgkin's disease, and non-Hodgkin's lymphoma.

Altretamine is sold under the trade name Hexalen®, and is also called hexamethylmelamine or HMM. It is used to treat ovarian cancer.

As used herein, "$C_1$-$C_{24}$alkyl" refers to straight or branched, saturated hydrocarbon groups containing from one to 24 carbon atoms. Representative alkyl groups include, but are not limited to, methyl, ethyl, n-propyl, isopropyl, n-butyl, isobutyl, sec-butyl, tert-butyl, n-pentyl, n-hexyl, n-heptyl, n-octyl, n-dodecyl, etc. Within the scope of the invention, "$C_1$-$C_{24}$alkyl" also encompasses "cycloalkyl," which refers to monocyclic, bicyclic, and tricyclic saturated hydrocarbons, for example, cyclopropyl, cyclobutyl, cyclopentyl, cyclobutyl, bicyclo[2.1.1]hexane, bicyclo[2.2.1]heptyl, adamantyl, and the like.

As used herein "polyethylene glycol," also referred to as "PEG," refers to polymers of the general formula $H(OCH_2CH_2)_nO$— or $H(OCH_2CH_2)_nOCH_3$, wherein n is at least 4. The preferred PEG has an average molecular weight of from about 200 to about 5000 Daltons, with a more preferred PEG from about 2000 to about 5000 Daltons.

As used herein, "pharmaceutically acceptable carrier or diluent" refers to solvents, dispersion media, coatings, bulking agents, stabilizing agents, antibacterial and antifungal agents, isotonic and absorption delaying agents, and the like, that are physiologically compatible. Examples of pharmaceutically acceptable carriers include one or more of water, saline, phosphate buffered saline, dextrose, glycerol, ethanol, sugars such as trehalose and sucrose, polyalcohols such as mannitol, sorbitol, mixtures of sugars and polyalcohols, and sodium chloride. Pharmaceutically acceptable carriers may further include auxiliary substances such as wetting or emulsifying agents, preservatives, and buffers.

As used herein, "pharmaceutical composition" refers to a composition suitable for administration in medical or veterinary use. Such compounds will preferably include a compound of the invention in combination with one or more carriers and/or diluents. Such compositions are also referred to as "formulations."

As used herein, "administering" refers to any means within the art by which compounds of the invention can be delivered to the patient. Preferred administration methods include local administration, that is, administration of the compounds of the invention directly to the location where the effect of the compounds is desired, and systemic administration. Examples of administration methods include, but are not limited to, oral, enteric, sublingual, sublavial, subcutaneous, nasal, intravenous, intraarterial, intramuscular, and intraperitoneal administration.

As used herein, "solid tumor" refers to a malignant tumor that is a localized mass of tissue. Examples of solid cancer tumors include lymphomas, sarcomas, and carcinomas and include breast cancer, brain cancer, bone cancer, colon cancer, pancreatic cancer, lung cancer, and the like.

As used herein, a "non-solid tumor cancer" refers most commonly to hematologic cancers, that is, malignant cancers of the blood. Examples of non-solid tumor cancers include chronic lymphocytic leukemia, Hodgkin's disease, indolent non-Hodgkin's lymphoma (T-cell lymphoma, B-cell lymphoma), multiple myeloma, and the like.

As used herein, "nanoparticles" refers to a particle having an average diameter of about 0.2 μm or less, preferably about 0.1 μm or less, as measured by Malvern Zetasizer.

EXPERIMENTAL SECTION

Preparation of 4-{5-[Bis-(2-chloro-ethyl)-amino]-1-methyl-1H-benzoimidazol-2-yl}-butyric acid methyl ester (bendamustine $C_1$ ester)

Method A: To a 1 L three neck, round bottom flask equipped with an overhead stirrer, condenser with nitrogen sweep, and thermocouple with temperature controller was charged 4-(5-amino-1-methyl-1H-benzoimidazol-2-yl)-butyric acid methyl ester (10.2 g, 41.2 mmol. 1.0 eq), and chloroacetic acid (81.9 g, 866 mmol), and 20 mL of dry tetrahydrofuran (THF). The slurry was stirred in a tap water bath to allow all of the solids to be dissolved. Borane-THF (288 mL, 288 mmol) was added slowly via an additional funnel over 25 minutes. When the addition of $BH_3$-THF was complete, the resulting reaction solution was stirred at room temperature for 1.5 hours and then heated at 58° C. using a heat mantle for 45 minutes. The reaction was cooled and held at room temperature overnight and then quenched with methanol (10 mL). The resulting solution was concentrated to approximately one-third weight by evaporation on the rotary evaporator and neutralized to pH 8-9 with an aqueous solution of sodium hydroxide in an ice-water bath. The solid was collected by vacuum filtration, washed with water (200 mL), then reslurried with a dilute aqueous solution of sodium bicarbonate (50 mL) for 20 minutes. Filtration was followed by drying with house vacuum at room temperature overnight, giving a tan solid (9.6 g, 63% yield, 93A % purity) $^1$H NMR (400 MHz, DMSO-d6) δ 7.32 (d, J=8.8 Hz, 1H), 6.92 (d, J=2.3 Hz, 1H), 6.78 (dd, J=8.8, 2.3 Hz, 1H), 3.70 (br s, 8H), 3.66 (s, 3H), 3.59 (s, 3H), 2.83 (t, J=7.4 Hz, 2H), 2.48 (t, J=7.4 Hz, 2H, overlapped partially with DMSO), 2.01 (quint, J=7.4 Hz, 2H); LC/MS (ESI, m/z) 372 (M+1), mp 60-63° C. dec.

Method B: To a 2 L three-neck glass vessel equipped with a heating mantle, thermocouple, condenser, nitrogen inlet/outlet, and overhead stirrer was charged bendamustine HCl (50.0 g, 126.7 mmol, 1.0 eq.), methanol (500 mL), and methanesulfonic acid (2.47 mL, 38.1 mmol). The reaction mixture was heated to reflux and stirred at 65° C. for one hour. The reaction solution was cooled to 40° C. and concentrated under vacuum. Water (500 mL) was added to the concentrated residue, and a saturated aqueous solution of $NaHCO_3$ (150 mL) was used to neutralize the mixture to pH 6 over 1.5 hours. The product was collected by filtration, washed with water (150 mL) and dried at 40° C. under vacuum, giving a white, powdery solid, 44.2 g (94% yield) with 98.4A % purity by HPLC.

Preparation of 4-{5-[Bis-(2-chloro-ethyl)-amino]-1-methyl-1H-benzoimidazol-2-yl}-butyric acid ethyl ester (bendamustine $C_2$ ester)

Method A: To a 1 L three-neck glass vessel equipped with a heating mantle, thermocouple, condenser, nitrogen inlet/outlet, and overhead stirrer was charged bendamustine HCl (30.0 g, 76 mmol, 1.0 eq.), ethanol (300 mL), and methanesulfonic acid (1.48 mL, 22.8 mmol). The reaction mixture was heated at 70° C. for one hour. The reaction solution was cooled to 40° C. and concentrated under vacuum. Water (300 mL) was added to the concentrated residue, and a saturated aqueous solution of $NaHCO_3$ (115 mL) was used to neutralize the mixture to pH 6 over 1.5 hours. The product was collected by filtration, washed with water (100 mL) and dried at 40° C. under vacuum, giving a white solid, 28.6 g (97% yield) with 99.2A % purity by HPLC. $^1$H NMR (400 MHz, DMSO-d6) δ 7.32 (d, J=8.8 Hz, 1H), 6.92 (d, J=2.3 Hz, 1H), 6.78 (dd, J=8.8, 2.3 Hz, 1H), 4.04 (quint, J=7.12 Hz, 2H), 3.70 (br s, 8H), 3.66 (s, 3H), 2.83 (t, J=7.4 Hz, 2H), 2.45 (t, J=7.4 Hz, 2H, overlapped partially with DMSO), 2.00 (quint, J=7.4 Hz, 2H), 1.18 (t, J=7.12 Hz, 3H).

Method B: To a 500 mL three-neck glass flask equipped with a heating mantle, thermocouple, condenser, nitrogen inlet/outlet, and overhead stirrer was charged 4-(5-amino-1-methyl-1H-benimidazol-2-yl)-butyric acid ethyl ester (6.4 g, 1.0 eq.), chloroacetic acid (42.5 g), and tetrahydrofuran (THF, 13 mL). The resulting mixture was stirred for 1.5 hours in a water bath at room temperature. Borane-THF (150 mL) was added over 20 minutes. Once the charge was complete, the reaction mixture was heated to 55-58° C. and stirred for 1.5 hours. In-process analysis by HPLC showed 94A % of the desired product. The reaction was cooled to room temperature and telescoped to the next step of hydrolysis to generate bendamustine.

Preparation of 4-{5-[Bis-(chloroethyl)-amino]-1-methyl-1H-benzimidazol-2-yl}butyric acid butyl ester (bendamustine $C_4$ ester)

A 250 mL three neck round bottom flask was equipped with an overhead stirrer, thermocouple, temperature controller and nitrogen sweep then charged with 10.0 g (25.34 mmol) of bendamustine hydrochloride, 1.9 g (2.35 mL, 25.6 mmol, 1.01 eq) of 1-butanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to a brown oil. The oil was triturated with 25 mL of MDC and the solid impurities were removed by vacuum filtration and washed with 25 mL of MDC. The filtrate was concentrated to dryness in vacuo to yield 9.5 g (22.8 mmol, 90%) of the product as a clear light brown oil with an HPLC purity of 94.5A%. $^1$H NMR (400 MHz, CDCl$_3$) δ 7.17 (d, J=8.76 Hz, 1H), 7.08 (d, J=2.32 Hz, 1H), 6.77 (dd, J=2.36, 8.8 Hz, 1H), 4.05 (t, J=6.76 Hz, 2H), 3.72 (m, 4H), 3.69 (s, 3H), 3.63 (m, 4H), 2.91 (t, J=7.4 Hz, 2H), 2.49 (t, J=7.1 Hz, 2H), 2.18 (m, 2H), 1.60 (m, 2H), 1.32 (m, 2H), 0.89 (t, J=4.56 Hz, 3H).

Preparation of 4-{5-[Bis-(chloroethyl)-amino]-1-methyl-1H-benzimidazol-2-yl}butyric acid hexyl ester (bendamustine $C_6$ ester)

Method A: A 250 mL three neck round bottom flask was equipped with an overhead stirrer, thermocouple, temperature controller and nitrogen sweep then charged with 10.0 g (25.34 mmol) of bendamustine hydrochloride, 2.62 g (3.22 mL, 25.6 mmol, 1.01 eq) of 1-hexanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to a brown oil. The oil was triturated with 25 mL of MDC and the solid impurities were removed by vacuum filtration and washed with 25 mL of MDC. The filtrate was concentrated to dryness in vacuo to yield 8.91 g (20.1 mmol, 79%) of the product as a clear light brown oil with an HPLC purity of 91.9A%. $^1$H NMR (400 MHz, CDCl$_3$) δ 7.17 (d, J=8.76 Hz, 1H), 7.08 (d, J=2.32 Hz, 1H), 6.77 (dd, J=2.36, 8.8 Hz, 1H), 4.05 (t, J=6.76 Hz, 2H), 3.72 (m, 4H), 3.69 (s, 3H), 3.63 (m, 4H), 2.91 (t, J=7.4 Hz, 2H), 2.49 (t, J=7.1 Hz, 2H), 2.18 (m, 2H), 1.60 (m, 2H), 1.32 (m, 6H), 0.89 (t, J=4.56 Hz, 3H).

Method B: A one liter 4-necked round bottom flask equipped with an overhead stirrer, thermocouple and nitrogen in/outlet was charged with 30 g (76.0 mmol) of bendamustine hydrochloride and 300 mL of dichloromethane. Agitation was begun and 10.6 mL (7.69 g, 76.0 mmol) of triethylamine was added via syringe then stirred for 15 minutes at room temperature before adding 1-ethyl-3-(3-dimethylaminopropyl) carbodiimide (EDAC, 21.86 g, 114 mmol) and n-hexyl alcohol (9.57 mL, 7.84 g, 76.8 mmol). The cloudy white reaction mixture became a clear solution after stirring for 20 minutes. Agitation was continued for 22.5 h at room temperature and 30° C. for one hour until reaction was complete by HPLC analysis. DI water (300 mL) was charged to quench the reaction and the pH was adjusted to 6 using 1N HCl. The layers were separated, aqueous was extracted with dichloromethane (100 mL), before combining the organic phases and drying over sodium sulfate. After filtration and concentration to dryness under vacuum a clear yellow oil was obtained which was purified by column chromatography (25 to 50% ethyl acetate in heptane). A total of 16.5 g (37.3 mmol, 49.1%) was recovered as a thick yellow oil with 99.1 A % purity by HPLC.

Preparation of 4-{5-[Bis-(chloroethyl)-amino]-1-methyl-1H-benzimidazol-2-yl}butyric aid octyl ester (bendamustine $C_8$ ester)

A 250 mL three neck round bottom flask was equipped with an overhead stirrer, thermocouple, temperature controller and nitrogen sweep then charged with 10.0 g (25.34 mmol) of bendamustine hydrochloride, 3.33 g (4.03 mL, 25.6 mmol, 1.01 eq) of 1-octanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to a brown oil. The oil was triturated with 25 mL of MDC and the solid impurities were removed by vacuum filtration and washed with 5 mL of MDC. The filtrate was concentrated to dryness in vacuo to yield 9.7 g (20.5 mmol, 81%) of the product as a clear light brown oil with an HPLC purity of 91.9A%. $^1$H NMR (400 MHz, CDCl$_3$) δ 7.17 (d, J=8.76 Hz, 1H), 7.08 (d, J=2.28 Hz, 1H), 6.77 (dd, J=2.4, 8.76 Hz, 1H), 4.05 (t, J=6.8 Hz, 2H), 3.72 (m, 4H), 3.69 (s, 3H), 3.63 (m, 4H), 2.91 (t, J=7.44 Hz, 2H), 2.49 (t, J=7.12 Hz, 2H), 2.18 (m, 2H), 1.60 (m, 2H), 1.32 (m, 10H), 0.89 (t, J=6.72 Hz, 3H).

Preparation of 4-{5-[Bis-(chloroethyl)-amino]-1-methyl-1H-benzimidazol-2-yl}butyric acid decyl ester (bendamustine $C_{10}$ ester)

Method A: A 250 mL three necked round bottom flask equipped with a stir bar, thermocouple and nitrogen in/outlet was charged with 10.0 g (25.3 mmol) of bendamustine hydrochloride, 4.9 mL (4.08 g, 25.6 mmol, 1.01 eq) of decyl alcohol, 5.3 g (25.6 mmol, 1.01 eq) of dicyclohexyl carbodiimide (DCC), 100 mL of dichloromethane and 0.31 g (2.53 mmol, 0.1 eq) of N,N-dimethylamino pyridine (DMAP). The reaction mixture was stirred at room temperature for 18 hours at which time an HPLC analysis indicated the reaction was complete. Solids were removed by vacuum filtration and the filtrate was washed with DI water (2×100 mL) and saturated sodium bicarbonate (1×100 mL) before being dried over sodium sulfate. The organic phase was filtered to remove the drying agent then concentrated to dryness in vacuo to give 9.6 g (19.2 mmol, 75.9%) of the desired product as a low melting white solid with an HPLC purity of 94.1A %. $^1$H NMR (400 MHz, CDCl$_3$) δ 7.17 (d, J=8.76 Hz, 1H), 7.08 (d, J=2.32 Hz, 1H), 6.77 (dd, J=2.4, 8.76 Hz, 1H), 4.05 (t, J=6.76 Hz, 2H), 3.72 (m, 4H), 3.69 (s, 3H), 3.63 (m, 4H), 2.91 (t, J=7.4 Hz, 2H), 2.49 (t, J=7.08 Hz, 2H), 2.18 (m, 2H), 1.60 (m, 2H), 1.32 (m, 14H), 0.87 (t, J=6.68 Hz, 3H).

Method B: A 250 mL 4-necked round bottom flask equipped with a magnetic stir bar, thermocouple and nitrogen in/outlet was charged with 10 g (25.3 mmol) of bendamustine hydrochloride and 100 mL of dichloromethane. Agitation was begun and 3.53 mL (2.56 g, 25.3 mmol) of triethylamine was added via syringe then stirred for 15 minutes at room temperature before adding 1-ethyl-3-(3-dimethylaminopropyl) carbodiimide (EDAC, 7.28 g, 38 mmol) and n-decyl alcohol (4.88 mL, 4.04 g, 25.5 mmol). The cloudy white reaction mixture became a clear solution after stirring for 20 minutes. Agitation was continued for 20 h at room temperature until reaction was complete by HPLC analysis. DI water (100 mL) was charged to quench the reaction and the pH was adjusted to 6-7 using 1N HCl. The layers were separated, aqueous was extracted with dichloromethane (25 mL), before combining the organic phases and drying over sodium sulfate. After filtration and concentration to dryness under vacuum a clear yellow oil was obtained which was purified by column chromatography (20 to 60% ethyl acetate in heptane). A total of 11.2 g (22.42 mmol, 88.6%) was recovered as a thick yellow oil with 98.9 A % purity by HPLC.

Preparation of 4-{5-[Bis-(chloroethyl)-amino]-1-methyl-1H-benzimidazol-2-yl}butyric aid dodecyl ester (bendamustine C$_{12}$ ester)

Method A: A 250 mL three neck round bottom flask was equipped with an overhead stirrer, thermocouple, temperature controller and nitrogen sweep then charged with 10.0 g (25.34 mmol) of bendamustine hydrochloride, 4.77 g (25.6 mmol, 1.01 eq) of 1-dodecanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to an off-white semi-solid. This solid was triturated with 25 mL of MDC and the solid impurities were removed by vacuum filtration and washed with 5 mL of MDC. The filtrate was concentrated to dryness in vacuo to yield 11.53 g (21.9 mmol, 86.4%) of the product as an off-white semisolid with an HPLC purity of 93.7A %.

Method B: A 20 liter jacketed cylindrical ChemGlass reaction vessel equipped with a thermocouple, heater/chiller, nitrogen inlet/outlet, addition funnel, and vacuum line was charged with the free base of bendamustine (374 g, 1.04 mol, 1.0 eq.), 1-ethyl-3-(3-dimethylaminopropyl) carbodiimide (EDAC, 300 g, 1.57 mol, 1.5 equivalents), and dichloromethane (DCM, 3.74 L, 10 volumes). While stirring 1-dodecanol (292.1 g, 1.57 mol, 1.5 equivalents) was added. The reaction mixture was heated to then stirred at 27° C. for 4 hours. The batch was cooled and held at 20° C. overnight. The batch was then washed with 3.75 L of water and the layers were separated. The aqueous portion was re-extracted with 1.2 L of dichloromethane, and the combined dichloromethane portions were dried over Na$_2$SO$_4$. After filtering to remove the drying agent, the filtrate was concentrated in vacuo to produce the product as a crude oil. Another batch of this reaction with 374 g of free base of bendamustine under the same conditions was carried out. The crude products from the two batches were combined, mixed with 4494 mL of heptanes and heated to 45-50° C. The resultant solution was allowed to slowly cool to room temperature, precipitating an off-white solid. The slurry was stirred overnight at room temperature and the solid was isolated at 10° C. by vacuum filtration. The wet cake was washed with 1 L of heptanes and reslurried with 2.5 L of heptane at 20-22° C. overnight. The product was collected by filtration and washed twice with 500 mL of heptanes each time. Drying the wet cakes overnight at 20-22° C. yielded 653 g (59% yield) of white solids at 99.0 A % by HPLC. $^1$H NMR (400 MHz, DMSO-d6) δ 7.32 (d, J=8.8 Hz, 1H), 6.92 (d, J=2.3 Hz, 1H), 6.78 (dd, J=8.8, 2.3 Hz, 1H), 3.99 (t, J=6.64 Hz, 2H), 3.70 (br s, 8H), 3.65 (s, 3H), 2.83 (t, J=7.4 Hz, 2H), 2.45 (t, J=7.4 Hz, 2H, overlapped partially with DMSO), 2.01 (quint, J=7.4 Hz, 2H), 1.54 (quint, J=6.9 Hz, 2H), 1.24 (m, 18H), 0.85 (t, J=6.8 Hz, 3H).

Preparation of 4-{5-[Bis-(chloroethyl)-amino]-1-methyl-1H-benzimidazol-2-yl}butyric acid tetradecyl ester (bendamustine C$_{14}$ ester)

Method A: A 500 mL three necked round bottom flask equipped with a stir bar, thermocouple and nitrogen in/outlet was charged with 10.0 g (25.3 mmol) of bendamustine hydrochloride, 6.5 g (30.4 mmol, 1.2 eq) of tetradecyl alcohol, 6.3 g (30.4 mmol, 1.2 eq) of dicyclohexyl carbodiimide (DCC), 100 mL of dichloromethane and 0.62 g (5.1 mmol, 0.2 eq) of N,N-dimethylamino pyridine (DMAP). The reaction mixture was stirred at room temperature for 20 hours at which time an HPLC analysis indicated the reaction was complete. Solids were removed by vacuum filtration and the wetcake was washed with 50 mL of dichloromethane before concentrating the filtrate to dryness in vacuo. The resultant light orange oil was triturated with 50 mL of dichloromethane and the undesired solids were removed by vacuum filtration. The filtrate was once again concentrated to dryness in vacuo to yield 16.5 g of a semi-solid which was shown by $^1$H NMR to contain tetradecanol and DMAP. The residue was chromatographed on 150 g of silica gel 60, 230-400 mesh eluting with 1500 mL of MDC, 1000 mL of 0.5% methanol/MDC and 2000 mL of 1% methanol/MDC collecting 100-150 mL fractions. Fractions containing the desired product were combined and concentrated to dryness in vacuo. The residue was again triturated with 30 mL of MDC and the undesired solids removed by filtration. The filtrate was concentrated in vacuo to yield 5.0 g (9.2 mmol, 36.4%) of the desired product as a light purple solid with a purity of 95.0A %.

Method B: To a 150 mL three-neck glass vessel equipped with a thermocouple, condenser, nitrogen inlet/outlet, and overhead mechanical stirrer was charged the free base of bendamustine (16.0 g, 44.6 mmol, 1.0 eq.), 1-ethyl-3-(3-dimethylaminopropyl) carbodiimide (EDAC, 9.42 g, 49.2 mol), 1-tetradecanol (10.6 g, 49.2 mmol) and dichloromethane (120 mL). The reaction mixture was stirred at 27° C. overnight. The reaction solution was cooled to room temperature and washed with 100 mL of water. While stirring, 1M aqueous HCl solution was added to adjust the pH of the aqueous layer to pH 3-4. The layers were separated. The aqueous portion was re-extracted with 100 mL of dichloromethane, and the combined dichloromethane portions were dried over MgSO$_4$. After filtering to remove the drying agent, the filtrate was concentrated in vacuo to produce the product as a waxy yellow solid. The solid was slurried in 80 mL of heptanes at room temperature overnight. The product was collected by filtration and dried, giving a white solid, 20.6 g (83.4% yield) with 97.2A % purity by HPLC. $^1$H NMR (400 MHz, DMSO-d6) δ 7.32 (d, J=8.8 Hz, 1H), 6.91 (d, J=2.3 Hz, 1H), 6.78 (dd, J=8.8, 2.3 Hz, 1H), 3.98 (t, J=6.64 Hz, 2H), 3.70 (br s, 8H), 3.66 (s, 3H), 2.83 (t, J=7.4 Hz, 2H), 2.45 (t, J=7.4 Hz, 2H, overlapped partially with DMSO), 2.01 (quint, J=7.3 Hz, 2H), 1.54 (m, 2H), 1.23 (m, 18H), 0.85 (t, J=7.12 Hz, 3H).

Preparation of 4-{5-[Bis-(chloroethyl)-amino]-1-methyl-1H-benzimidazol-2-yl}butyric acid pentadecyl ester (bendamustine C$_{15}$ ester)

A 250 mL three neck round bottom flask was equipped with an overhead stirrer, thermocouple, temperature controller and nitrogen sweep then charged with 10.0 g (25.34 mmol) of bendamustine hydrochloride, 5.85 g (25.6 mmol, 1.01 eq) of pentadecanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to an off-white solid. This solid was triturated with 25 mL of MDC and the solid impurities were removed by vacuum filtration and washed with 5 mL of MDC. The filtrate was concentrated to dryness in vacuo to yield 10.8 g (19.0 mmol, 75%) of the product as an off-white solid with an HPLC purity of 94.6A %. $^1$H NMR (400 MHz, CDCl$_3$) δ 7.17 (d, J=8.76 Hz, 1H), 7.08 (d, J=2.32 Hz, 1H), 6.78 (dd, J=2.4, 8.76 Hz, 1H), 4.05 (t, J=6.8 Hz, 2H), 3.72 (m, 4H), 3.69 (s, 3H), 3.63 (m, 4H), 2.91 (t, J=7.4 Hz, 2H), 2.49 (t, J=7.08 Hz, 2H), 2.18 (m, 2H), 1.60 (m, 2H), 1.32 (m, 24H), 0.88 (t, J=6.68 Hz, 3H).

Preparation of 4-{5-[Bis-(chloroethyl)-amino]-1-methyl-1H-benzimidazol-2-yl}butyric acid hexadecyl ester (bendamustine C$_{16}$ ester)

A 250 mL three neck round bottom flask was equipped with an overhead stirrer, thermocouple, temperature controller and nitrogen sweep then charged with 10.0 g (25.34 mmol) of bendamustine hydrochloride, 6.2 g (25.6 mmol, 1.01 eq) of hexadecanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was washed with saturated aqueous sodium bicarbonate solution (2×100 mL), DI water (1×100 mL) and brine (1×100 mL) before drying over sodium sulfate, filtering and concentrating to dryness in vacuo to an off-white solid. This solid was triturated with 25 mL of MDC and the solid impurities were removed by vacuum filtration and washed with 5 mL of MDC. The filtrate was concentrated to dryness in vacuo to yield 13.1 g (22.5 mmol, 88.8%) of the product as an off-white solid with an HPLC purity of 94.0A %. $^1$H NMR (400 MHz, CDCl$_3$) δ 7.17 (d, J=8.76 Hz, 1H), 7.08 (d, J=2.32 Hz, 1H), 6.78 (dd, J=2.36, 8.72 Hz, 1H), 4.05 (t, J=6.8 Hz, 2H), 3.72 (m, 4H), 3.69 (s, 3H), 3.63 (m, 4H), 2.91 (t, J=7.4 Hz, 2H), 2.49 (t, J=7.08 Hz, 2H), 2.18 (m, 2H), 1.60 (m, 2H), 1.32 (m, 26H), 0.88 (t, J=6.68 Hz, 3H).

Preparation of 4-{5-[Bis-(2-chloro-ethyl)-amino]-1-methyl-1H-benzoimidazol-2-yl}-butyric acid Oleoyl ester (bendamustine C$_{18}$ ester)

Method A: To a 250 mL, three neck, round bottom flask equipped with an overhead stirrer, condenser with nitrogen sweep, heating mantle with temperature controller and thermocouple was charged 1-octadecanol (50 g, 185 mmol, 7.3 eq). The solid was heated to melt it before adding slowly 4-(5-amino-1-methyl-1H-benzoimidazol-2-yl)-butyric acid (10 g, 25.3 mmol. 1.0 eq) and sulfuric acid (0.5 mL). The resulting slurry was stirred at 70° C. for 6 hours and then cooled to 56° C., where methylene chloride (150 mL) was added. The reaction mixture was cooled to room temperature and washed with water (100 mL). After phase separation, another extraction was performed with methylene chloride (100 mL). The organic phases were combined and dried over MgSO$_4$. The drying agent was removed by filtration. The filtrate was concentrated and subjected to SFC isolation. A white solid was obtained from evaporation of solvent in the SFC fractions under reduced pressure and dried with house vacuum at room temperature for 5 days, giving 1.2 g of the desired product in 7.1% yield and with 95.4A % purity. $^1$H NMR (400 MHz, CDCl3) δ 7.18 (d, J=8.8 Hz, 1H), 7.09 (d, J=2.3 Hz, 1H), 6.78 (dd, J=8.8, 2.4 Hz, 1H), 4.05 (t, J=6.8 Hz, 2H), 3.74 (m, 7H), 3.62 (m, 4H), 2.93 (t, J=7.4 Hz, 2H), 2.49 (t, J=7.1 Hz, 2H), 2.22 (quint, J=7.1 Hz, 2H), 1.60 (quint, J=7.1 Hz, 2H), 1.28 (m, 30H), 0.88 (t, J=7.1 Hz, 3H); LC/MS (ESI, m/z) 610 (M+1).

Method B: To a 500 mL, three neck, round bottom flask equipped with a stir bar, nitrogen sweep, and thermocouple was charged with bendamustine HCl (5.04 g, 12.8 mmol), 1-octadecanol (4.15 g, 15.3 mmol), N,N'-Dicyclohexylcarbodiimide (DCC, 3.17 g, 15.4 mmol), 4-Dimethylaminopyridine (DMAP, 0.31 g, 2.56 mmol) and methylene chloride (250 mL). The resulting slurry was stirred at room temperature for 16 hours. A solid was produced and removed from the reaction mixture by filtration. The filtrate was washed with water (150 mL). After phase separation, the organic phase dried over MgSO$_4$. The drying agent was removed by filtration and the filtrate was concentrated and subjected to ISCO chromatographic purification with a mixture of EtOAc and heptanes, giving a white solid 5.68 g (73% yield) with 99A % purity.

Preparation of 4-{5-[Bis-(chloroethyl)-amino]-1-methyl-1H-benzimidazol-2-yl}butyric acid docosyl ester (bendamustine C$_{22}$ ester)

A 250 mL three necked round bottom flask equipped with a stir bar, thermocouple and nitrogen in/outlet was charged with 5.0 g (12.7 mmol) of bendamustine hydrochloride, 4.2 g (12.9 mmol, 1.01 eq) of docosyl alcohol, 2.7 g (12.9 mmol, 1.01 eq) of dicyclohexyl carbodiimide (DCC), 50 mL of dichloromethane (MDC) and 0.16 g (1.27 mmol, 0.1 eq) of N,N-dimethylamino pyridine (DMAP). The reaction mixture was stirred at room temperature overnight at which time an HPLC analysis indicated the reaction was complete. Solids were removed by vacuum filtration and the wetcake was washed with 50 mL. Two alternate purification procedures were developed. The filtrate was washed with DI water (2×150 mL), dried over sodium sulfate, filtered and concentrated to dryness in vacuo. The resultant waxy residue was chromatographed on 80 g of silica gel 60, 230-400 mesh eluting with a gradient beginning with 100% MDC, then 0.5% methanol/MDC and finally 1% methanol/MDC collecting 100-150 mL fractions. Fractions containing the desired product were combined and concentrated to dryness in vacuo. The residue was again triturated with 20 mL of MDC and the undesired solids removed by filtration. The filtrate was concentrated in vacuo to yield 3.65 g (5.5 mmol, 43.1%) of the desired product as a waxy white solid with a purity of 95.7A %. $^1$H NMR (400 MHz, CDCl$_3$) δ 7.17 (d, J=8.72 Hz, 1H), 7.08 (d, J=2.28 Hz, 1H), 6.78 (dd, J=2.36, 8.72 Hz, 1H), 4.05 (t, J=6.76 Hz, 2H), 3.72 (m, 4H), 3.70 (s, 3H), 3.63 (m, 4H), 2.91 (t, J=7.44 Hz, 2H), 2.49 (t, J=7.08 Hz, 2H), 2.18 (m, 2H), 1.60 (m, 2H), 1.32 (m, 38H), 0.88 (t, J=6.64 Hz, 3H).

Preparation of 4-{5-[Bis-(chloroethyl)-amino]-1-methyl-1H-benzimidazol-2-yl}butyric acid 2-dodecyl ester (branched bendamustine C$_{12}$ ester)

A 250 mL three neck round bottom flask was equipped with an overhead stirrer, thermocouple, temperature controller and nitrogen sweep then charged with 10.0 g (25.34 mmol) of bendamustine hydrochloride, 4.77 g (5.75 mL, 25.6 mmol, 1.01 eq) of 2-dodecanol, 5.3 g (25.6 mmol, 1.01 eq) of dicyclohexylcarbodiimide (DCC), 100 mL of MDC and 0.31 g (2.54 mmol, 0.1 eq) of DMAP. The reaction was stirred at room temperature overnight at which time an in process analysis indicated the reaction was complete. Solids were removed by vacuum filtration and washed with 25 mL of MDC. The filtrate was diluted with 200 mL of MDC then washed with 4% aqueous sodium bicarbonate solution (1×500 mL) before drying over sodium sulfate, filtering and concentrating to dryness in vacuo to an off-white solid. This solid was triturated with 25 mL of MDC and the solid impurities were removed by vacuum filtration and washed with 5 mL of MDC. The filtrate was concentrated to dryness in vacuo to yield the crude product which was shown to contain residual 2-dodecanol by $^1$H NMR. The crude product was chromatographed using 100 g of silica gel 60, 230-400 mesh, eluting with first 1 L of heptanes, then 500 mL of 3:1 heptane/EtOAc, 500 of 2:1 heptane/EtOAc and finally 500 mL of 1:1 heptane/EtOAc collecting 100 mL fractions. Product containing fractions were combined and concentrated to dryness in vacuo to yield 5.35 g (10.16 mmol, 40%) of the product as a light purple viscous oil with an HPLC purity of 99.5A %. $^1$H NMR (400 MHz, DMSO-d$_6$) δ 7.31 (d, J=8.76 Hz, 1H), 6.93 (d, J=2.28 Hz, 1H), 6.78 (dd, J=2.36, 8.76 Hz, 1H), 4.8 (m, 1H), 3.7 (s, 8H), 3.65 (s, 3H), 2.82 (t, J=7.4 Hz, 2H), 2.42 (t, J=7.36 Hz, 2H), 2.00 (m, 2H), 1.50 (m, 2H), 1.25 (s, b, 16H), 1.14 (d, J=6.24 Hz, 2H), 0.84 (t, J=6.68 Hz, 3H).

Preparation of Bendamustine C$_{12}$ Ester

A 20 liter jacketed cylindrical ChemGlass reaction vessel equipped with thermocouple, heater/chiller, nitrogen inlet, addition funnel, condenser, and vacuum line was charged with a slurry of 428 g (1.10 mmol) of pretreated bendamustine hydrochloride in 10 volumes of trace GC analysis grade methylene chloride. Agitation was set at 100 RPM and the jacket was set at 20° C. To this mixture was added diisopropylethylamine (213 ml, 1.1 eq) via an addition funnel over 10 minutes. After a 34 minute hold, melted dodecanol (227 g, 1.1 eq) was added in one portion. After an 11 minute hold, EDCI (320.3 g, 1.5 eq) was added to the batch. The resulting clear yellow solution was agitated for 23.5 hours at ~20° C. At this point, an IPC indicated 0.54% starting starting material remained. Ten volumes of water were added and the reaction was agitated for an additional 15 minutes. The lower organic layer was drained, filtered through a 5 micron filter cartridge, and the filter cartridge was rinsed with 1 volume of GC analysis grade methylene chloride. The methylene chloride solution was concentrated in vacuo to afford the crude product as a viscous yellow oil.

Five volumes of filtered n-heptane were added to the oil and the mixture was concentrated in vacuo to remove residual methylene chloride to yield 615 g of crude solids with in 92.9 wt % translating to a 98.0% yield. Final purity was 98.4% on a dry basis.

Purification of Bendamustine C$_{12}$ Ester

Crude CEP-40125 (1100 g API, 1250 g crude) was taken up in n-heptane (6 volumes) and transferred to a 20 liter jacketed cylindrical ChemGlass reaction vessel equipped with thermocouple, heater/chiller, nitrogen inlet, condenser, and vacuum line. The slurry was warmed to 40° C. to dissolve all solids. Upon reaching 32.6° C., dissolution occurred. The reaction mixture was then cooled to 17.7° C. over 2.5 hours, at which point the product precipitated. The reaction mixture was then re-warmed to 23° C. to dissolve fine particles over 26 minutes, and cooled to 4° C. over 2 hours. The solids were filtered through a sealed filter and washed with 2 volumes of cold n-heptane over 4.5 hours. An IPC indicated 0.20% residual dodecanol. The solids were dried under vacuum for 24 hours at 30° C. to constant weight to afford 1018 g CEP-40125 in 98.3% purity, representing a 92.5% yield.

Preparation of 4-{5-[Bis-(chloroethyl)-amino]-1-methyl-1H-benzimidazol-2-yl}butyric acid 5-decyl ester (branched bendamustine C$_{10}$ ester)

A 250 mL three neck round bottom flask was equipped with an overhead stirrer, thermocouple, temperature controller and nitrogen sweep then charged with 3.0 g (7.6 mmol) of bendamustine hydrochloride, 1.21 g (7.7 mmol, 1.01 eq) of 5-decanol, 1.59 g (7.7 mmol, 1.01 eq) of dicyclohexylcarbodiimide (DCC), 30 mL of 1,2-ethylene dichloride (EDC) and 0.1 g (0.76 mmol, 0.1 eq) of DMAP. The reaction was stirred at 75° C. for five days until an in process analysis indicated the reaction was complete. Solids were removed by vacuum filtration and washed with 5 mL of EDC. The filtrate was washed with 4% aqueous sodium bicarbonate solution (1×50 mL) before drying over sodium sulfate, filtering and concentrating to dryness in vacuo. The residue was combined with the residue from a 10 g batch run carried out under the same conditions and the combined batches were chromatographed. The chromatography was carried out using 100 g of silica gel 60, 230-400 mesh, eluting with first 2 L of heptanes, then 1 L of 3:1 heptane/EtOAc and 1 L of 2:1 heptane/EtOAc collecting 100 mL fractions. Product containing fractions were combined and concentrated to dryness in vacuo to yield 3.97 g (7.96 mmol, 24.2%) of the product as a clear yellow oil with an HPLC purity of 99.4A %. $^1$H NMR (400 MHz, DMSO-d$_6$) δ 7.31 (d, J=8.76 Hz, 1H), 6.93 (d, J=2.28 Hz, 1H), 6.78 (dd, J=2.40, 8.80 Hz, 1H), 4.8 (m, 1H), 3.7 (s, 8H), 3.65 (s, 3H), 2.83 (t, J=7.4 Hz, 2H), 2.44 (t, J=7.36 Hz, 2H), 2.02 (m, 2H), 1.48 (m, 4H), 1.25 (s, b, 10H), 0.84 (m, 6H).

Preparation of 4-{5-[Bis-(chloroethyl)-amino]-1-methyl-1H-benzimidazol-2-yl}butyric acid cyclohexyl ester A 250 mL three neck round bottom flask was equipped with an overhead stirrer, thermocouple, temperature controller and nitrogen sweep then charged with 10 g (25.34 mmol) of bendamustine hydrochloride, 2.56 g (2.7 mL, 25.6 mmol, 1.01 eq) of cyclohexanol, 5.3 g (25.6 mmol, 1.01 eq) of dicyclohexylcarbodiimide (DCC), 100 mL of MDC and 0.31 g (2.54 mmol, 0.1 eq) of DMAP. The reaction slurry was stirred at RT for 18 h until an in process analysis indicated the reaction was complete. Two new major product peaks were observed. Solids were removed by vacuum filtration and washed with 5 mL of MDC. The filtrate was washed with 4% aqueous sodium bicarbonate solution (2×100 mL) before drying over sodium sulfate, filtering and concentrating to dryness in vacuo to yield a yellow oil with some solids present. $^1$H NMR analysis indicated residual DMAP and cyclohexanol was along with DCC by-products were present in addition to the desired product. The residue was slurried with 50 mL of MDC to remove residual cyclohexanol then concentrated in vacuo and chromatographed. The chromatography was carried out using 50 g of silica gel 60, 230-400 mesh, eluting with 1:1 heptane/EtOAc collecting 100 mL fractions. Product containing fractions were combined and concentrated to dryness in vacuo to yield 3.11 g (7.06 mmol, 27.9%) of the product as an off-white solid with an HPLC purity of 97.8A %. $^1$H NMR (400 MHz, DMSO-d$_6$) δ 7.31 (d, J=8.76 Hz, 1H), 6.93 (d, J=2.28 Hz, 1H), 6.77 (dd, J=2.40, 8.80 Hz, 1H), 4.65 (m, 1H), 3.7 (s, 8H), 3.65 (s, 3H), 2.83 (t, J=7.4 Hz, 2H), 2.44 (t, J=7.36 Hz, 2H), 2.00 (m, 2H), 1.76 (m, 4H), 1.65 (m, 2H), 1.33 (m, b, 6H).

Preparation of 4-{5-[Bis-(2-chloro-ethyl)-amino]-1-methyl-1H-benzoimidazol-2-yl}-butyric acid PEG-2000 ester (bendamustine PEG-2000 ester)

To a 100 mL three-neck glass vessel equipped with a stir bar, thermocouple, condenser, and nitrogen inlet/outlet was charged bendamustine hydrochloride (2.0 g, 5.1 mmol, 1.0 eq.) and dichloromethane (30 mL). Triethyl amine (0.71 mL, 5.1 mmol) was added to the slurry at 22° C. and stirred for 20 minutes. Methoxypolyethylene glycol 2000 (PEG-OMe-2000, 12.2 g, 6.1 mmol) and 1-ethyl-3-(3-dimethylaminopropyl) carbodiimide (EDAC, 1.5 g, 7.6 mol) were added. The reaction mixture was stirred at 22° C. for 5.5 hours, at this point addition of PEG-OMe-2000 (1.0 g) was followed by stirring for 3 days through weekend. Water (20 mL) was added and pH was adjusted to pH 5-6 by adding 1M hydrochloric acid. The phases separated slowly. The aqueous portion was re-extracted with 20 mL of dichloromethane, and the combined dichloromethane portions were dried over MgSO$_4$. After filtering to remove the drying reagent, the filtrate was concentrated in vacuo to produce the product as a waxy solid. The solid was slurried in 10 mL of heptanes at room temperature. The product was collected by filtration and dried at 30° C. under vacuum, giving a white and powdery solid, 11.7 g (99% yield) with 97.9A % purity by HPLC. $^1$H NMR (400 MHz, DMSO-d6) δ 7.32 (d, J=8.6 Hz, 1H), 6.92 (d, J=2.2 Hz, 1H), 6.78 (dd, J=8.8, 2.2 Hz, 1H), 4.12 (t, J=4.8 Hz, 2H), 3.70 (m, 12H), 3.60 (m, 3H), 3.51 (m, 224H), 3.43 (m, 4H), 3.32 (m, 58H), 2.84 (t, J=7.4 Hz, 2H), 2.45 (2H, overlapped partially with DMSO), 2.01 (quint, J=7.3 Hz, 2H).

Preparation of 4-{5-[Bis-(2-chloro-ethyl)-amino]-1-methyl-1H-benzoimidazol-2-yl}-butyric acid PEG-5000 ester (bendamustine PEG-5000 ester)

To a 50 mL three-neck glass vessel equipped with a stir bar, thermocouple, condenser, and nitrogen inlet/outlet was charged bendamustine hydrochloride (0.5 g, 1.27 mmol, 1.0 eq.) and dichloromethane (15 mL). Triethyl amine (0.18 mL, 1.28 mmol) was added to the slurry at 22° C. and stirred for 20 minutes along with methoxypolyethylene glycol 5000 (PEG-OMe-5000, 6.33 g, 1.27 mmol) and, 1-ethyl-3-(3-dimethylaminopropyl) carbodiimide (EDAC, 0.36 g, 1.88 mol). The reaction mixture was stirred at 22° C. overnight. Water (20 mL) was added and pH was adjusted to pH 3-4 by adding 1M hydrochloric acid. The phases separated slowly. The aqueous portion was re-extracted with 10 mL of dichloromethane. The combined dichloromethane portions were washed with brine (20 mL) and dried over MgSO$_4$. After filtering to remove the drying agent, the filtrate was concentrated in vacuo to produce the product as a waxy solid. The solid was slurried in 20 mL of heptanes at room temperature. The product was collected by filtration and dried at 30° C. under vacuum, giving a white and powdery solid, 5.24 g (77% yield) with 99A % purity by HPLC. $^1$H NMR (400 MHz, DMSO-d6) δ 7.38 (d, J=12 Hz, 1H), 6.91 (d, J=2.4 Hz, 1H), 6.82 (d, J=10 Hz, 1H), 4.12 (t, J=4.7 Hz, 2H), 3.72 (br s, 8H), 3.68 (m, 5H), 3.59 (m, 3H), 3.51 (m, 436H), 3.42 (m, 3H), 3.31 (m, 28H), 2.88 (t, J=7.4 Hz, 2H), 2.45 (t, 2H, overlapped partially with DMSO), 2.01 (quint, J=7.3 Hz, 2H).

General Procedure for Transesterification of Bendamustine Methyl Ester

To a 50 mL three-neck glass vessel equipped with a stir bar, thermocouple, condenser with a Dean-Stark trap, and nitrogen inlet/outlet was charged bendamustine methyl ester (0.5 g, 1.27 mmol, 1.0 eq.), catalyst (0.05-1.4 eq.), an appropriate solvent (5-15 volumes), and an excess of dodecanol (5-10 eq.). The resulting reaction mixture was heated to reflux and monitored by HPLC. The results under varied conditions are summarized below.

| Catalyst | Catalyst (eq) | Solvent | Solvent Volumes | Alcohol Equivs | Temp (° C.) | Dean-Stark Trap | Time (h) | Start material (HPLC A %) | Product (HPLC A %) |
|---|---|---|---|---|---|---|---|---|---|
| CH$_3$SO$_3$H | 1.40 | NA | NA | 2.50 | 30 | N | 3 | 3.8 | 94.5 |
| CH$_3$SO$_3$H | 1.40 | DCM | 10 | 2.50 | 30 | N | 47 | 22.0 | 76.2 |
| CH$_3$SO$_3$H | 1.40 | Toluene | 10 | 2.50 | 70 | N | 24 | 19.3 | 69.7 |
| I$_2$ | 0.25 | Toluene | 5 | 2.50 | 75 | N | 7 | 96.0 | 0.2 |
| TiO(acac)$_2$ | 0.05 | Xylenes | 10 | 1.01 | 130 | N | 7 | 92.7 | 4.0 |
| TiO(acac)$_2$ | 0.10 | Xylenes | 5 | 10.0 | 130 | N | 6 | 10.5 | 85.5 |
| TiO(acac)$_2$ | 0.10 | Xylenes | 5 | 10.0 | 160 | N | 5 | 9.0 | 78.6 |
| TiO(acac)$_2$ | 0.10 | Xylenes | 15 | 5.00 | 160 | Y | 6 | 1.0 | 97.0 |
| H$_2$SO$_4$ | 0.5 | Toluene | 10 | 5.0 | 100 | N | 23 | 78.9 | 13.5 |
| DMAP | 0.5 | Toluene | 10 | 5.0 | 100 | N | 23 | 83 | 0 |
| p-TSA | 0.5 | Xylenes | 10 | 5.0 | 130 | N | 21 | 67.2 | 15.6 |
| Sm(Oi-Pr)$_3$ | 0.5 | THF | 10 | 5.0 | 25-45 | N | 27 | 2.6 | 90.5 |
| Superbase | 0.5 | THF | 10 | 5.0 | 25-45 | N | 27 | 3.3 | 49.8 |
| Sm(Oi-Pr)$_3$ | 0.1 | Xylenes | 15 | 5.0 | 160 | N | 8 | 72.8 | 24.3 |
| Sm(Oi-Pr)$_3$ | 0.5 | THF | 10 | 5.0 | 40 | N | 16 | 95.8 | 2.5 |
| TiO(acac)$_2$ | 0.05 | Xylenes | 15 | 5.0 | 150 | Y | 3 | 0.3 | 96.9 |
| TiO(acac)$_2$ | 0.05 | Toluene | 15 | 5.0 | 105 | N | 70 | 78.9 | 15.9 |
| TiO(acac)$_2$ | 0.10 | Toluene | 15 | 5.0 | 115 | Y | 22 | ND | 96.4 |

-continued

| Catalyst | Catalyst (eq) | Solvent | Solvent Volumes | Alcohol Equivs | Temp (° C.) | Dean-Stark Trap | Time (h) | Start material (HPLC A %) | Product (HPLC A %) |
|---|---|---|---|---|---|---|---|---|---|
| TiO(acac)$_2$ | 0.05 | Toluene | 15 | 5.0 | 130 | N | 24 | 83.2 | 4.1 |
| TiO(acac)$_2$ | 0.05 | Toluene | 15 | 5.0 | 115 | Y | 21 | 0.4 | 97.7 |

Preparation of Bendamustine Hydrochloride Amides

4-{5-[Bis-(2-chloro-ethyl)-amino]-1-methyl-1H-benzoimidazol-2-yl}-N-decyl-butylamine (bendamustine C$_{10}$ amide)

A 250 mL three neck round bottom flask equipped with a stir bar, thermocouple, cooling bath, 60 mL pressure equalizing dropping funnel and nitrogen in/outlet was charged with 10.0 g (25.3 mmol) of bendamustine hydrochloride, 10.6 g (27.8 mmol) of HATU and 100 mL of N,N-dimethylformamide (DMF). To this stirred yellow solution was added 4.41 mL (3.27 g, 25.3 mmol) of N,N-diisopropylethylamine (DIPEA). An exotherm to 27.1° C. was noted and the solution became a darker yellow. The reaction was cooled to 6.6° C. where a solution of 6.2 mL (4.59 g, 35.5 mmol) of DIPEA, 5.11 mL (4.1 g, 25.6 mmol) of decyl amine in 20 mL of DMF was added drop-wise over 13 min at 2.7-7.6° C. Once addition was complete the reaction was allowed to stir at <10° C. for 1.5 hours at which time an in process analysis indicated the reaction was complete. The batch was quenched onto 200 mL of DI water and extracted with ethyl acetate (2×175 mL). The organic phases were combined, washed with 10% sodium hydrogen phosphate (1×200 mL), 8% aqueous sodium bicarbonate (1×200 mL) and brine (1×200 mL) before concentrating to dryness in vacuo to give a sticky white solid. This solid was triturated with heptanes (75 mL) and became a flowable solid which was isolated by vacuum filtration. The wetcake was dried in a vacuum oven at 25° C. overnight to yield 13.33 g (25.3 mmol, 100%) of the desired product as a white solid with an HPLC purity of 98.01A %. $^1$H NMR (400 MHz, DMSO-d6) δ 7.72 (s, b, 1H), 7.33 (d, J=8.76 Hz, 1H), 6.91 (d, J=2.28 Hz, 1H), 6.80 (dd, J=2.36, 8.8 Hz), 3.7 (s, 8H), 3.66 (s, 3H), 3.01 (q, J=6.8, 12.68, 2H), 2.79 (t, J=7.44 Hz, 2H), 2.18 (t, J=7.36 Hz, 2H), 1.95 (m, 2H), 1.36 (m, 2H), 1.22 (s, b, 14), 0.84 (t, J=6.68 Hz, 3H).

4-{5-[Bis-(2-chloro-ethyl)-amino]-1-methyl-1H-benzoimidazol-2-yl}-N-tetradecyl-butryamide (bendamustine C$_{14}$ amide)

A 250 mL three neck round bottom flask equipped with a stir bar, thermocouple, cooling bath, 60 mL pressure equalizing dropping funnel and nitrogen in/outlet was charged with 10.0 g (25.3 mmol) of bendamustine hydrochloride, 10.6 g (27.8 mmol) of HATU and 100 mL of N,N-dimethylformamide (DMF). To this stirred yellow solution was added 4.41 mL (3.27 g, 25.3 mmol) of N,N-diisopropylethylamine (DIPEA). An exotherm to 27.1° C. was noted and the solution became a darker yellow. The reaction was cooled to 3.3° C. where a solution of 6.2 mL (4.59 g, 35.5 mmol) of DIPEA, 5.75 gf (25.6 mmol) of tetradecyl amine in 40 mL of DMF was added drop-wise over 6 min at <10° C. Once addition was complete the reaction became very thick and difficult to stir. It was transferred to a 500 mL three neck round bottom flask equipped with an overhead stirrer and thermocouple, then stirred at RT for three hours at which time an in process analysis indicated the reaction was complete. The batch was quenched onto 400 mL of DI water and extracted with ethyl acetate (2×300 mL), the organic phases were combined, washed with 10% sodium hydrogen phosphate (1×300 mL), 8% aqueous sodium bicarbonate (1×300 mL) and brine (1×300 mL) before drying over sodium sulfate, filtering and concentrating to dryness in vacuo. The residue was purified by chromatography using 100 g of silica gel 60, 230-400 mesh, eluting with 1% MeOH/MDC (2 L), 2.5% MeOH/MDC (1 L) and 5% MeOH/MDC (1 L) collecting ~100 mL fractions. The product containing fractions were combined and concentrated to dryness in vacuo to yield 7.86 g (14.6 mmol, 57.6%) of the desired product as a white solid with an HPLC purity of 97.3A %. $^1$H NMR (400 MHz, DMSO-d6) δ 7.72 (s, b, 1H), 7.33 (d, J=8.84 Hz, 1H), 6.91 (d, J=2.22 Hz, 1H), 6.80 (dd, J=2.36, 8.84 Hz), 3.71 (s, 8H), 3.70 (s, 3H), 3.01 (q, J=6.8, 12.68, 2H), 2.79 (t, J=7.44 Hz, 2H), 2.18 (t, J=7.36 Hz, 2H), 1.97 (m, 2H), 1.36 (m, 2H), 1.28 (s, b, 22), 0.84 (t, J=7.04 Hz, 3H).

4-{5-[Bis-(2-chloro-ethyl)-amino]-1-methyl-1H-benzoimidazol-2-yl}-N-octadecyl-butyramide (bendamustine C$_{18}$ amide)

A 250 mL three neck round bottom flask equipped with a stir bar, thermocouple, cooling bath, 60 mL pressure equalizing dropping funnel and nitrogen in/outlet was charged with 10.0 g (25.3 mmol) of bendamustine hydrochloride, 10.6 g (27.8 mmol) of HATU and 100 mL of N,N-dimethylformamide (DMF). To this stirred yellow solution was added 4.41 mL (3.27 g, 25.3 mmol) of N,N-diisopropylethylamine (DIPEA). An exotherm to 27.1° C. was noted and the solution became a darker yellow. The reaction was cooled to 2.0° C. where a suspension of 6.2 mL (4.59 g, 35.5 mmol) of DIPEA, 7.65 g (25.6 mmol) of octadecyl amine in 0 mL of DMF was added via pipette. Once addition was complete the reaction became very thick and difficult to stir. It was warmed to room temperature and the magnetic stir bar was replaced with an overhead stirrer. The batch was stirred at RT overnight after which time an in process analysis indicated the reaction was complete. The batch was quenched onto 300 mL of DI water and extracted with dichloromethane (2×150 mL). The organic phases were combined, washed with 10% sodium hydrogen phosphate (1×300 mL), 8% aqueous sodium bicarbonate (1×300 mL) and brine (1×300 mL) before drying over sodium sulfate, filtering and concentrating to dryness in vacuo. The residue was purified by chromatography using 100 g of silica gel 60, 230-400 mesh, eluting with 1% MeOH/MDC (2 L), 2.5% MeOH/MDC (1 L) and 5% MeOH/MDC (1 L) collecting ~100 mL fractions. The product containing fractions were combined and concentrated to dryness in vacuo to yield 5.11 g (8.38 mmol, 33%) of the desired product as a white solid with an HPLC purity of 90.9A %. The major impurity was shown to be the C-16 amide which results from an impurity in the starting amine. $^1$H NMR (400 MHz, DMSO-d6) δ

7.72 (s, b, 1H), 7.33 (d, J=8.84 Hz, 1H), 6.91 (d, J=2.22 Hz, 1H), 6.80 (dd, J=2.36, 8.84 Hz), 3.71 (s, 8H), 3.70 (s, 3H), 3.01 (q, J=6.8, 12.68, 2H), 2.79 (t, J=7.44 Hz, 2H), 2.18 (t, J=7.36 Hz, 2H), 1.97 (m, 2H), 1.36 (m, 2H), 1.28 (s, b, 30H), 0.85 (t, J=6.32 Hz, 3H).

(S)-2-(4-{5-[Bis-(2-chloro-ethyl)-amino]-1-methyl-1H-benzoimidazol-2-yl}-butyrylamino)-propionic acid methyl ester A 250 mL three neck round bottom flask equipped with a stir bar, thermocouple, cooling bath, addition funnel and nitrogen in/outlet was charged with 10 g (25.3 mmol) of bendamustine hydrochloride, 10.6 g (27.8 mmol) of HATU and 100 mL of DMF. The batch was cooled to 1.9° C. where 8.8 mL (6.54 g, 50.6 mmol) of DIPEA was added over 2 minutes. The reaction exothermed to 9° C. and became orange. A solution of 3.57 g (25.6 mmol) of L-alanine methyl ester hydrochloride and 6.2 mL (4.57 g, 35.4 mmol) of DIPEA in 20 mL of DMF was added drop-wise over 10 minutes at 4.9-5.7° C. The reaction was slowly warmed to RT over one hour and stirred for three hours at which time an in process assay indicated the reaction was complete. The batch was quenched onto 400 mL of 1:1 ethyl acetate/DI water. The layers were separated, the organic was washed with 10% sodium hydrogen phosphate (1×200 mL), 8% sodium bicarbonate 91×200 mL) and brine (1×200 mL), before drying over sodium sulfate, filtering and evaporating to dryness in vacuo. The residue was purified by chromatography using 100 g of silica gel 60, 230-400 mesh, eluting with 1% MeOH/MDC (3 L), 2.5% MeOH/MDC (1 L) and 5% MeOH/MDC (500 mL) collecting ~100 mL fractions. The product containing fractions were combined and concentrated to dryness in vacuo to yield 7.1 g (16.0 mmol, 63.3%) of the desired product as a white solid with an HPLC purity of 97.4A %. $^1$H NMR (400 MHz, DMSO-d6) δ 8.25 (d, J=6.92 Hz), 1H), 7.40 (d, J=8.84 Hz, 1H), 6.92 (d, J=2.2 Hz, 1H), 6.86 (dd, J=2.32, 8.88 Hz), 4.25 (q, 1H), 3.72 (s, 8H), 3.71 (s, 3H), 3.62 (s, 3H), 2.87 (t, J=7.48 Hz, 2H), 2.25 (t, J=7.52 Hz, 2H), 1.99 (m, 2H), 1.26 (d, J=7.32 Hz, 3H).

General Procedure for Preparing Solution Formulations of Bendamustine Esters of the Invention:

A stock solution of the bendamustine ester of the invention was dissolved in a 60/40 (v/v) mixture of dimethylacetamide ("DMA") and Solutol® HS-15 at about 100 mg/mL concentration. The mixture was stirred at room temperature until dissolved. The resulting stock solution, which was stable for several months, was diluted with 0.9% saline to the desired concentration and dosed within about 2 hours.

Bendamustine $C_{14}$ Ester Solution Formulation:

A stock solution was prepared by dissolving 320.1 mg of bendamustine $C_{14}$ ester in 4 mL of a 60/40 (v/v) mixture of DMA and Solutol® HS-15. The mixture was stirred for about 2 hours until dissolved. Prior to dosing, the stock solution was diluted by removing 1.00 mL of the stock solution and adding 16.20 mL saline and stirring for 5 minutes at room temperature. The resulting formulation was 3 mg-equ/mL bendamustine.

Pretreatment to Remove Residual Ethanol:

Bendamustine hydrochloride (277 g) was charged into a 5 L evaporation flask followed by 2 volumes of DI water and 5 volumes of acetone. The solvents were distilled under vacuum at a maximum temperature of 40° C. over 5.5 hours. An additional 5 volumes of acetone were added and the resulting slurry was rotated at atmospheric pressure on the rotary evaporator at 35° C. for 15 minutes. The batch was then filtered through a sealed sintered glass funnel and the resulting white solids were rinsed with 2 volumes of acetone. The solids were transferred to a drying tray and dried at 40° C. to constant weight for 17 hours before isolating 266 g (96.0%) of product in 99.8A % purity with KF of 0.26%.

General Procedure for Preparing Human Serum Albumin ("HSA") Nanoparticle Formulations of Bendamustine Esters of the Invention Nanoparticles were formed from an O/W emulsion using dichloromethane and HSA as a surfactant. The oil phase was prepared by dissolving the desired amount of bendamustine ester in dichloromethane at a concentration of about 120 mg/mL. The water phase was prepared by dissolving 2-4× the amount of HSA (w/w base on the bendamustine ester) in 5-15× the volume of water (w/w based on dichloromethane). Typically, mannitol was added to the aqueous phase at 5-10% to make the solution isotonic for injection and to provide a pharmaceutically appropriate product post lyophilization. The O/W emulsion was formed by emulsifying the oil phase and the water phase using and IKA hand-held homogenizer at medium intensity for about 30 seconds. The nanoparticles were formed by processing the crude O/W emulsion through a Microfluidizer® high pressure homogenizer (5 passes at about 30,000 psi) to provide 50-100 nm sized particles, as measured using dynamic light scattering (Malvern Zetasizer). The solvent was removed under vacuum and the resulting concentrate was either lyophilized or stored frozen prior to dosing. These formulations exhibited good physical and chemical stability.

The lyophilized nanoparticles were reconstituted and analyzed using cryo-Transmission Electron Microscopy (c-TEM). The majority of the nanoparticles were 20-40 nm solid spheres that were readily dispersed in water. A minority of particles were in the 125 nm range. The particles all had a smooth surface.

Bendamustine $C_{12}$ Ester HSA Nanoparticles:

An oil phase was prepared by dissolving 600 mg of bendamustine $C_{12}$ ester in 5 mL of dichloromethane. The oil phase was emulsified with an aqueous phase comprised of 60 mL deionized ("DI") water, 2.4 g HSA (lyophilized solid from Sigma-Aldrich, St. Louis, Mo.) and 6.6 g mannitol using an IKA Ultra-Turrex hand held homogenizer to obtain a coarse emulsion. This emulsion was passed five times through a Microfluidics M-110P high pressure homogenizer at about 30,000 psi. The dichloromethane was removed from the resulting nanoparticle suspension using a rotory-evaporator and the resulting aqueous suspension was diluted to bring the total volume to 100 mL with DI water. This suspension was then portioned in 10 mL aliquots into 30 mL serum vials and lyophilized.

Bendamustine $C_{12}$ Ester HSA Nanoparticles with Poly-Lactic Glycolic Acid (PLGA):

An oil phase was prepared by dissolving 300 mg of bendamustine $C_{12}$ ester and 500 mg of PLGA (50/50 lactic to glycolic with a MW of 7,000-17,000; Aldrich Part #719897) in 2.5 mL of dichloromethane. The oil phase was emulsified with an aqueous phase comprised of 30 mL DI water, 1.2 g HSA (lyophilized solid from Sigma-Aldrich) and 3.3 g mannitol using and IKA Ultra-Turrex hand held homogenizer to obtain a coarse emulsion. This emulsion was passed five times through a Microfluidics M-110P high pressure homogenizer at about 30,000 psi. The dichloromethane was removed from the resulting nanoparticle using a roto-evaporator and the resulting aqueous suspension was diluted to bring the total volume to 50 mL with DI water. The resulting nanoparticles had a particle size of 90.5 nm ($Z_{avg}$) as measured by Malvern Zetasizer. This suspension was then portioned in 10 mL aliquots into 30 mL serum vials and lyophilized.

Bendamustine $C_{12}$ Ester HSA Nanoparticles from Concentrate:

A series of nanoparticle formulations were prepared with a PEG coating, which was reported in the literature (Alexis, F., *Molecular Pharmaceutics*, 5, (2008), 505-515) to provide a "stealth" coating and aid in the particle ability to avoid the body's immune system. The incorporation of PEG was done by using a PEG based surfactant (copolymer of PEG and poly lactic acid) instead of HSA or using bioconjugate chemistry to covalently attach PEG groups to the free $NH_2$ groups on the surface of the HSA nanoparticles. Both systems showed increased plasma circulation times in PK studies.

Bendamustine $C_{12}$ Ester HSA Nanoparticles with Polyethyleneglycol (PEG) Coating:

An oil phase was prepared by dissolving 600 mg of bendamustine $C_{12}$ ester in 5 mL of dichloromethane. The oil phase was emulsified with an aqueous phase comprised of 60 mL DI water, 2.4 g HSA (lyophilized solid from Sigma-Aldrich) and 6.6 g mannitol using and IKA Ultra-Turrex hand held homogenizer to obtain a coarse emulsion. This emulsion was passed five times through a Microfluidics M-110P high pressure homogenizer at ~30,000 psi. The dichloromethane was removed from the resulting nanoparticle suspension using a roto-evaporator and the resulting aqueous suspension was diluted to bring the total volume to 50 mL with DI water. The suspension of nanoparticles were then diluted into 200 mL of a 100 mM pH 8.5 borate buffer and the particle size and zeta-potential of the resulting nanoparticles were measured using a Malvern Zetasizer. The nanoparticles had a particle size of 78.9 nm ($Z_{avg}$) and a surface charge of −13.0 mV. The suspension was stirred and 150 mg of methoxy-$PEG_{5,000}$-n-hydroxysuccinimide ester (Laysan Polymer) was added. The reaction was mixed for ~90 minutes at room temperature and the particle size and zeta-potential were re-measured. The nanoparticles particle size was found to be 83.6 nm (Zavg) and the zeta-potential was −7.35 mV. The nanoparticles were buffer exchanged and concentrated with a 6.6% (wt/wt) mannitol solution and a 50,000 MWCO diafiltration cartridge. This suspension was then portioned in 10 mL aliquots into 30 mL serum vials and lyophilized.

Bendamustine $C_{12}$ Ester Nanoparticles with Poly-Lactic Glycolic Acid (PLGA) and polyoxyEthylene Lactic Acid Copolymer (PELA) Surfactant:

An oil phase was prepared by dissolving 300 mg of bendamustine $C_{12}$ ester and 500 mg of PLGA (50/50 lactic to glycolic with a MW of 7,000-17,000; Aldrich Part #719897) in 2.5 mL of dichloromethane. The oil phase was emulsified with an aqueous phase comprised of 30 mL DI water, 0.6 g a copolymer of PEG-5,000-poly lactic acid 1,000 (copolymer prepared using procedure from A. Lucke, *Biomaterials*, 21, (2000), 2361-2370) and 3.3 g mannitol using and IKA Ultra-Turrex hand held homogenizer to obtain a coarse emulsion. This emulsion was processed for 5 minutes through a Microfluidics M-110P high pressure homogenizer at 30,000 PSI. The dichloromethane was removed from the resulting nanoparticle suspension using a roto-evaporator and the resulting aqueous suspension was diluted to bring the total volume to 50 mL with DI water. The resulting nanoparticles had a particle size of 248.0 nm ($Z_{avg}$) as measured by Malvern Zetasizer. This suspension was then portioned in 10 mL aliquots into 30 mL serum vials and lyophilized.

Bendamustine $C_{12}$ Ester HSA Nanoparticles from Concentrate:

An oil phase was prepared by dissolving 4.8 g of Bendamustine $C_{12}$ ester in 13.4 g of dichloromethane. The oil phase was emulsified with an aqueous phase comprised of 111 g deionized ("DI") water and 9 g HSA using an IKA Ultra-Turrex hand held homogenizer to obtain a coarse emulsion. This emulsion was passed five times through a Microfluidics M-110P high pressure homogenizer at about 30,000 psi. The resulting nanoemulsion concentrate was stabilized by adding 12 g NaCl and mixing until dissolved. Stabilization can also be achieved using other methods known in the art, for example, other salts, controlled heating, and/or pH adjustments. Cross-linking with, for example, glutaraldehyde, can also assist in preventing aggregation.

The dichloromethane was removed from the resulting nanoparticle suspension using a rotory-evaporator. The resulting aqueous suspension was mixed with 12 g of sucrose and DI water was added to bring the total weight to 480 g. This suspension was then portioned in 7.5 mL aliquots into 20 mL serum vials and lyophilized.

Figure 21:
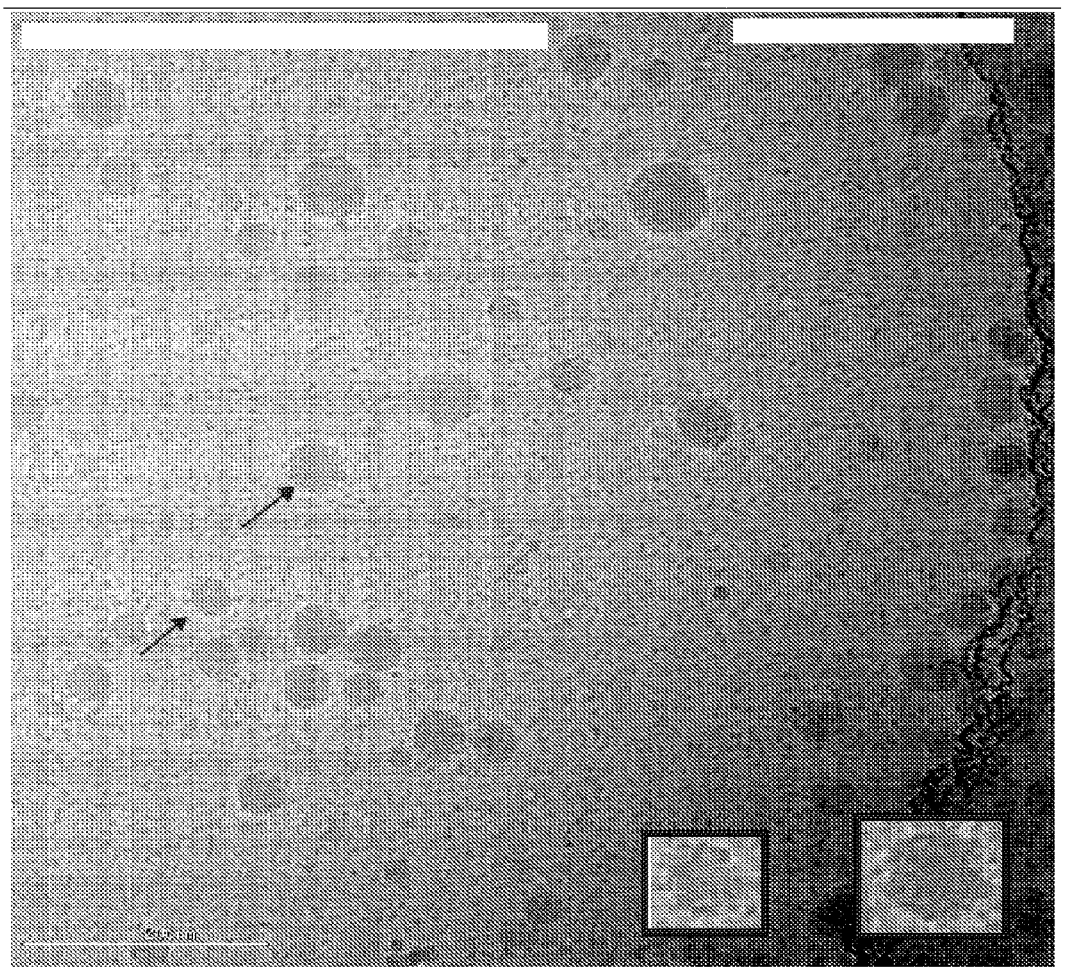
FIG. 21 depicts a representative nanoparticle embodiment of the invention at a magnification of 52,000×. Observed in the sample are: spherical particles that appear evenly denser than the surrounding buffer (left-most arrows), small particles in the background (right-most arrow). Insets show the two particles denoted by the left-most arrows at a larger scale. Distance between crosses in the left image is 28 nm, between crosses in the right inset is 43 nm. Scale Bar: 200 nm.
Figure 22:
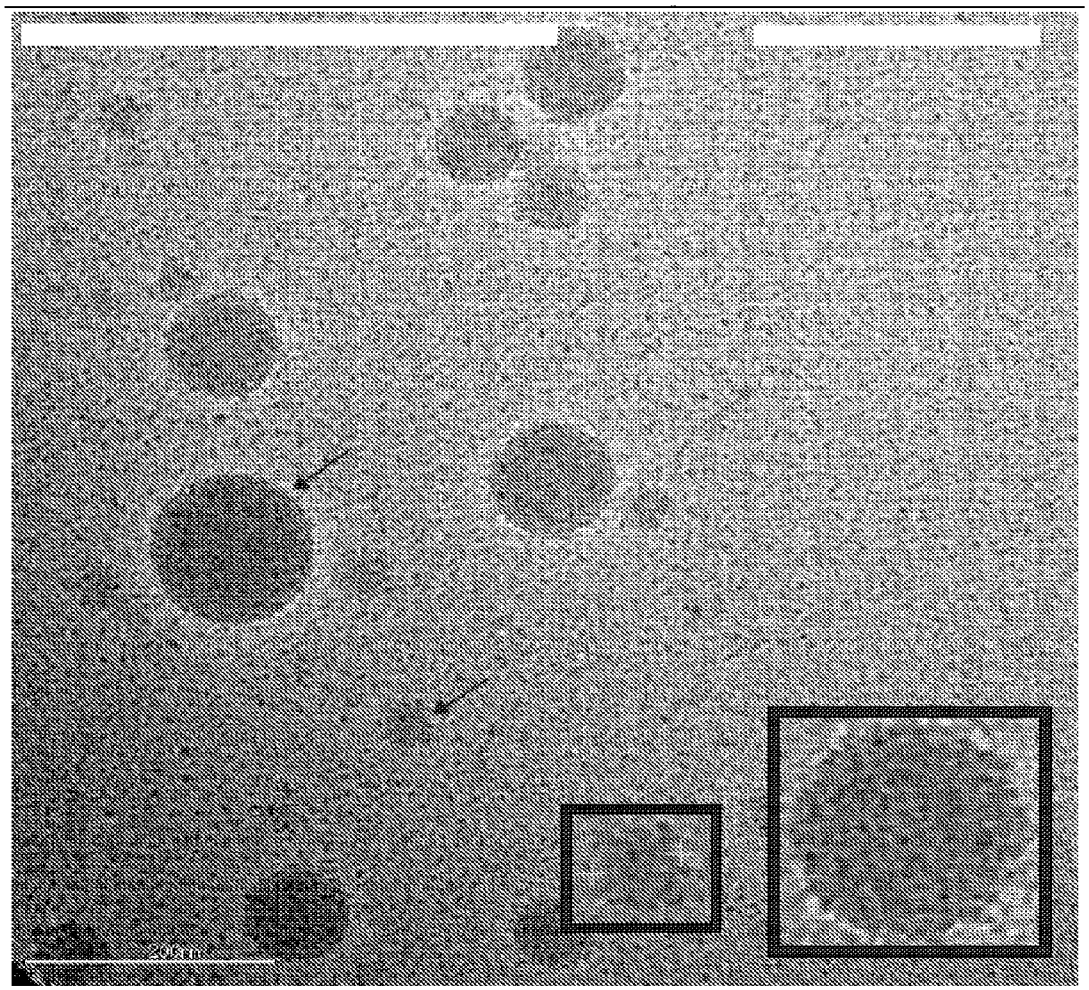
FIG. 22 depicts a representative nanoparticle embodiment of the invention at a magnification of 52,000×. Observed in the sample are: spherical particles that appear evenly denser than the surrounding buffer (left-most arrows), small particles in the background (right-most arrow). Insets show the two particles denoted by the left-most arrows at a larger scale. Distance between crosses in the left image is 28 nm, between crosses in the right inset is 43 nm. Scale Bar: 200 nm.

Solutions of the HSA nanoparticles exhibited a slow particle size increase with time. Some solutions reached ~200 nm in size within 12-24 hours as measured by dynamic light scattering. The nature of this increase was investigated using c-TEM in order to determine if the nanoparticles were aggregating or if excess protein in the formulation was adding on to the surface of the particle to increase the particle size. A vial of lyophilized nanoparticles was reconstituted and imaged using c-TEM (FIG. 21). The same vial of nanoparticles was allowed to stand at room temperature for 24 hours then re-imaged (FIG. 22). The original sample contained spherical particles with a size distribution between 25-60 nm. The aged sample exhibited an increase in size distribution to 35-130 nm with no sign of particle aggregation. Both samples contain a population of 1-3 nm particles which are consistent with "free" protein. These results suggest that "free" HSA is adding to the surface of the nanoparticles while in solution to cause a slow increase in particle size. Several strategies may be employed to mitigate this process including change in pH, change in osmolarity, solvent addition and diafiltration to remove excess protein.

Protocol for Preparing Tumor Cell Isolates:

Charles River Labs athymic nude mice bearing MDA-MB-231 breast carcinoma cell line subcutaneous xenografts ($5 \times 10^6$ cells in matrigel) were sacrificed to make a tumor isolate. Using sterile instruments and working aseptically, the tumors were removed from the euthanized animal. The tumor was placed in a 50 mL sterile conical tube and 5 mL of trypsin was added. The tumor was cut into small pieces and incubated at 37° C. for 30 minutes. After incubation, a cell strainer was placed on a second, sterile, 50 mL conical tube and the contents of the first tube were placed in the cell strainer. The tissue was forced through the filter using the flat end of a syringe plunger. The cell strainer was washed with 5 mLs of media containing FBS. The cells were spun down and the supernatant was discarded. The cells were resuspended in 20 mLs of complete media containing P/S and placed in a 75 cm flask. This data is set forth in Table 1.

General Procedure for MTS Cell Assay:

Human carcinoma cells (2,000 cells/well) were incubated with the desired concentration of the test molecule (0-200 µM) for 72 hours. The cells were then incubated with MTS solution (Promega) for 1-2 hours, and the compounds effects on cell proliferation was determined by measuring the absorbance at 490 nm. Cell growth was expressed as a percent of the appropriate control (placebo). This data was used to calculate an $IC_{50}$ for each compound. All data reported was the mean±SE of three independent experiments. This data is set forth in Table 1.

TABLE 1

[Structure: benzimidazole with bis(2-chloroethyl)amino group and N-methyl, 2-(butyl-COOR₁) substituent]

| R₁ | MB-231 (HBC) IC$_{50}$ (μM) | $R^2$ | H-460 (NSCLC) IC$_{50}$ (μM) | $R^2$ |
|---|---|---|---|---|
| —OH | 13-16 | 0.88-0.95 | 4-26 | 0.83-0.95 |
| —CH$_3$ | 66 | 0.95 | 1.2 | 0.9 |
| —C$_4$H$_9$ | 13.3 | 0.91 | 15.73 | 0.9 |
| —C$_6$H$_{13}$ | 43.7 | 0.93 | 7.4 | 0.89 |
| —C$_8$H$_{17}$ | 53.1 | 0.86 | 49 | 0.89 |
| —C$_{10}$H$_{21}$ | 38.89 | 0.87 | 23.76 | 0.93 |
| —C$_{12}$H$_{25}$ | 33.3 | 0.78 | 28.8 | 0.69 |
| —C$_{14}$H$_{29}$ | >200 | 0.83 | 129.9 | 0.87 |
| —C$_{15}$H$_{31}$ | >200 | 0.93 | >200 | 0.66 |
| —C$_{16}$H$_{33}$ | >200 | 0.85 | 77.8 | 0.9 |
| —C$_{18}$H$_{37}$ | N.D. | N.D. | 29 | |

$R^2$ = coefficient of determination

Figure 20:
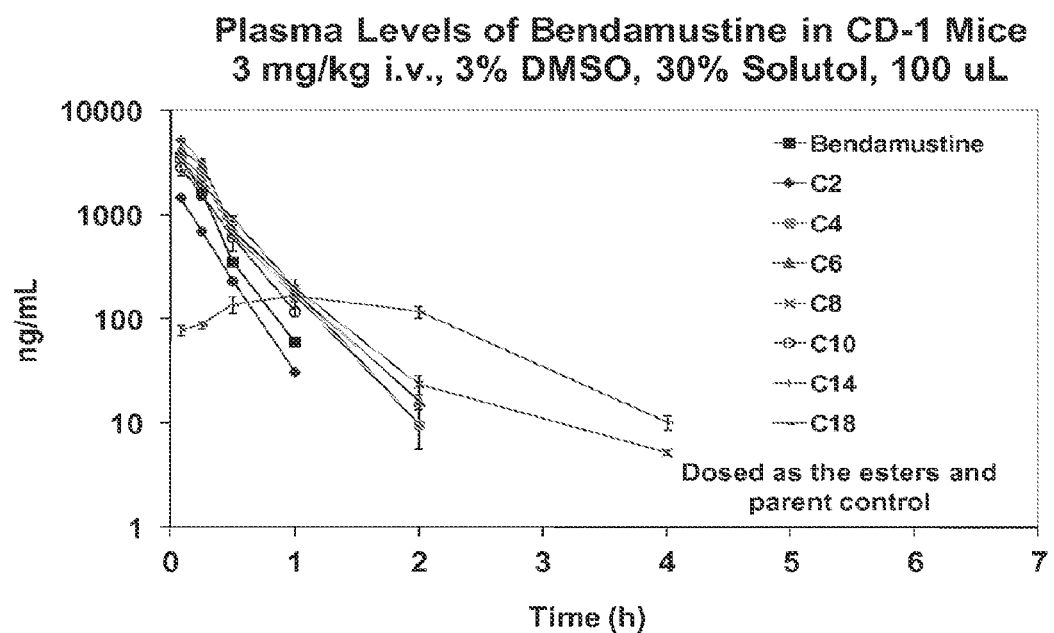
FIG. 20 depicts plasma levels of bendamustine in CD-1 mice after dosing embodiments of the invention at 3 mg/kg i.v., 3% DMSO, 30% Solutol.

The foregoing biological data is also depicted in FIG. 1. Plasma levels of bendamustine after administration of the foregoing esters are depicted in FIG. 20.

Tumor Efficacy

Figure 2:
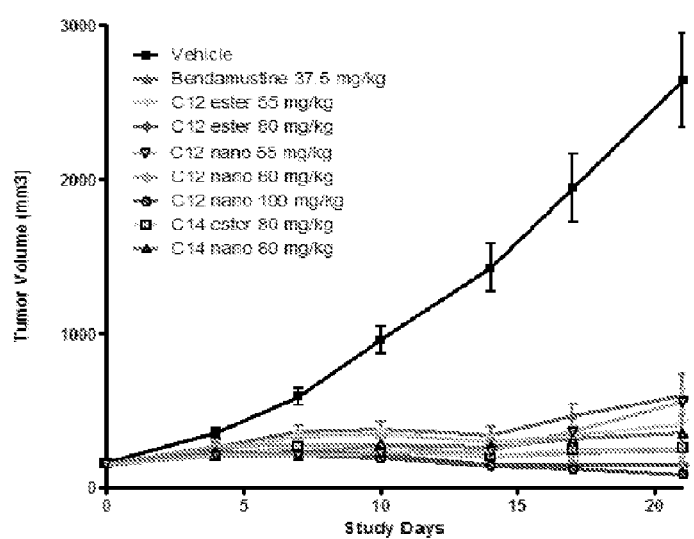
FIG. 2 depicts the effects of bendamustine hydrochloride and certain embodiments of the invention on tumor volumes of mice bearing MDA-MB-231 xenografts.

Procedure for Nude Mouse MDA-MB-231 Tumor Efficacy Study:

Charles River Labs athymic nude mice were subcutaneous injected with 5×10$^6$ human tumor cells in matrigel. The tumor volume was monitored until an average tumor size of ~150 mm$^3$ was obtained in the mouse population The mice were then randomized in to one of the nine treatment groups (summarized in table below) with a population of 10 mice per group (n=10). Each of the formulations was dosed at 100 μL fixed volume via tail vein injection on day 1 and day 2 of the study. Mice were weighed and the tumor volume measured every 3-4 days for 3 weeks of the study duration. This data is depicted in Table 2 and FIG. 2.

Procedure for Nude Mouse H460 Tumor Efficacy Study:

H460 tumor cells (large cell lung cancer) were cultured in RPMI-1640 medium containing 10% FBS and with 95% air and 5% CO$_2$ at 37° C. When reaching to 80-90% confluent, the cells were detached by 0.25% Trypsin-EDTA solution within 5-10 minutes, neutralized with fresh cultured medium, and counted by a cell counter (Cellometer, Auto T4 by Nexcelom). 2×10$^6$ cells/100 ul in the mix of medium and Matrigel (1:1 ratio) solution was injected into right back flank of each nu/nu mouse. The implanted mice were monitored and measured with electric calipers. The study started when the tumors reached ~150 mm$^3$ in size. The mice were measured and randomized into 9 groups with 10 mice in each group per the below table:

TABLE 2

Summary of Tumor Efficacy Data Against MB-231 of Bendamustine (BM1), Bendamustine C$_{12}$ Ester, and Bendamustine C$_{14}$ Ester: % Tumor Inhibition, % Morbidity/Mortality, and Tumor and Plasma Levels.

| | | | % Tumor | | Levels at 1 hour (ng/mL) | | | |
| | | | | | Ester | | BM1 | |
| | | mg/kg | Inh. | % Morbidity/Mortality | Tumor | Plasma | Tumor | Plasma |
|---|---|---|---|---|---|---|---|---|
| Solution | BM1 | 37.5 | 77 | 10/0 | — | — | 558 | 906 |
| | C$_{12}$ | 55 | 84 | 40/0 | 425 | 0 | 1932 | 4110 |
| | C$_{12}$ | 80 | 94 | 80/20 | 644 | 16 | 4400 | 11650 |
| | C$_{14}$ | 80 | 90 | 40/0 | 396 | 14 | 7 | 21 |
| HSA nanoparticle | C$_{12}$ | 55 | 79 | 10/0 | 261 | 2 | 1845 | 6307 |
| | C$_{12}$ | 80 | 91 | 70/40 | 762 | 292 | 7320 | 18757 |
| | C$_{12}$ | 100 | 97 | 100/70 | 1565 | 39 | 15050 | 23933 |
| | C$_{14}$ | 80 | 86.5 | 60/0 | 10430 | 5727 | 5500 | 15110 |

| Tumor Efficacy Dosing Groups | | |
|---|---|---|
| Compound | Formulation | Dose (mg/kg Free Base Eq.) |
| Vehicle Control | Solution | NA |
| Bendamustine HCl | TREANDA | 37.5 |
| Bendamustine $C_{12}$ ester | Solution | 55 |
| Bendamustine $C_{12}$ ester | Solution | 80 |
| Bendamustine $C_{12}$ ester | Nanoparticle | 55 |
| Bendamustine $C_{12}$ ester | Nanoparticle | 80 |
| Bendamustine $C_{12}$ ester | Nanoparticle | 100 |
| Bendamustine $C_{14}$ ester | Solution | 80 |
| Bendamustine $C_{14}$ ester | Nanoparticle | 80 |

The formulations were administrated as 100 μL dose volume through tail vein injection within 30 minutes after compounds were formulated. All the mice were weighed and tumors measured twice weekly. At the last day of the study, plasma, tumor, lung, liver, spleen, left kidney, brain and legs were collected and quickly frozen for further analysis two hours post-dosing. The results are shown in Table 3.

TABLE 3

Summary of Tumor Efficacy Data Against H-460 of Bendamustine (BM1), Bendamustine $C_{12}$ Ester, and Bendamustine $C_{14}$ Ester: % Tumor Inhibition, % Morbidity/Mortality, and Tumor and Plasma Levels.

| | | % Tumor | | | Levels at 1 hour (ng/mL) | | | |
|---|---|---|---|---|---|---|---|---|
| | | | | | Ester | | BM1 | |
| | | mg/kg | Inh. | % Morbidity/Mortality | Tumor | Plasma | Tumor | Plasma |
| Solution | BM1 | 37.5 | 41.5 | 0/0 | — | — | 1472 | 1550 |
| | $C_{12}$ | 55 | 66 | 20/20 | 163 | 12 | 3760 | 6943 |
| | $C_{12}$ | 80 | 75 | 100/50 | 206 | 12 | 5180 | 13600 |
| | $C_{14}$ | 80 | 81 | 100/40 | 8570 | 32233 | 4650 | 24633 |
| HSA nanoparticle | $C_{12}$ | 55 | 47 | 10/0 | 154 | 0 | 1761 | 4743 |
| | $C_{12}$ | 80 | 64 | 40/0 | 321 | 0 | 2997 | 8053 |
| | $C_{12}$ | 100 | 70 | 50/0 | 437 | 2 | 3565 | 12386 |
| | $C_{14}$ | 80 | 40 | 10/0 | 4570 | 3648 | 1872 | 4467 |

Pharmacokinetic Study Experimentals

Procedure for Nude Mouse Tumor Efficacy PK Group:

A portion of the tumor bearing mice were dosed as a satellite PK group. Each group was dosed as described for the tumor efficacy group, however the PK group was euthanized and tissue samples collected at 1, 3 and 6 hours post dosing on day 2. The tissues collected included blood, lung, liver and tumor. Samples were analyzed for bendamustine HCl and the corresponding ester analogue as described in the LC-MS protocol section.

LC-MS Experimental Protocol for PK Studies:

Plasma and other tissues were prepared for high performance liquid chromatography (HPLC)/mass spectrometric analysis according to a standard protocol following protein precipitation with acetonitrile containing an internal standard. The samples were then analyzed for both bendamustine HCl and bendamustine esters of the invention and alprenolol (internal standard) via HPLC coupled with tandem mass spectrometry. Tissue samples were homogenized in sodium phosphate buffer and the value obtained from the assay was multiplied by 3 to correct for dilution during processing.

Animal Dosing Protocol for PK Studies:

Adult animals (Charles River, Kingston, N.Y.; n=3 or 4/time point) were used in all experiments. The mice or rats were not fasted overnight prior to IV dose administration via the lateral tail vein. IV doses were administered in a fixed dose volume of 100 μL in mice or a dose volume of 1 mL/kg in rats. The mice were sacrificed by decapitation and trunk blood was collected into heparinized tubes at the sampling times stipulated. For blood collection, each rat (unanesthetized) was placed in a clear Plexiglas® restraining tube, and blood samples (approximately 0.25 mL) were drawn from a lateral tail vein into heparinized collection tubes at the sampling times stipulated. (Note: No pre-dose samples were obtained.) The exception to this procedure was the last sampling time in which the rats were sacrificed by decapitation and trunk blood was obtained rather than blood via a tail vein. The blood samples were placed on wet ice until centrifuged to separate plasma. The plasma fraction was transferred into clean, dry tubes, frozen on dry ice and stored at approximately −20° C. pending analysis. Whole brains and other highly perfused organs (liver, lung, spleen, kidney and heart) were rapidly removed at the predetermined time points and frozen on dry ice. All tissue samples were also stored at approximately −20° C. pending analysis.

Pharmacokinetic Analysis:

The plasma concentration data for all mice and rats were entered into Excel spreadsheets in preparation for pharmacokinetic analysis. Mean pharmacokinetic parameters were estimated by non-compartmental analysis (Gibaldi and Perrier 1982) of the plasma concentration versus time data using WinNonlin software (Professional Version 4.1, Pharsight Corporation, Palo Alto, Calif.). The terminal rate constant for elimination from plasma ($\beta$) was estimated by linear regression of the terminal portion of the semi-logarithmic plasma concentration versus time curve. The apparent terminal half-life (t½) was calculated as 0.693 divided by β. The area under the plasma concentration versus time curve from time zero to the time of the last measurable concentration (AUC0-t) after a single dose was determined by the linear trapezoidal rule. The area from zero to infinity (AUC0-∞) was calculated as the sum of AUC0-t and the area extrapolated from the last measurable concentration to infinity (Clast/β). Concentrations pre-dose were all assumed to be zero for the purpose of calculation of the AUC. Any concentration that was below the limit of quantification (BLQ) after the last quantifiable sampling time was considered to be an empty value for the purpose of calculation of the AUC; it was treated as zero for the calculation of the mean concentration for a given sampling time.

Data from the pharmacokinetic studies is depicted in Tables 4-17.

TABLE 4

| Plasma | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 5.7 | ND | 6.0 | ND |
| $AUC_{0-t}$, ng * h/mL | 66885 | ND | 55296 | ND |
| $AUC_{0-\infty}$, ng * h/mL | 67131 | ND | 55417 | ND |

Figure 8:
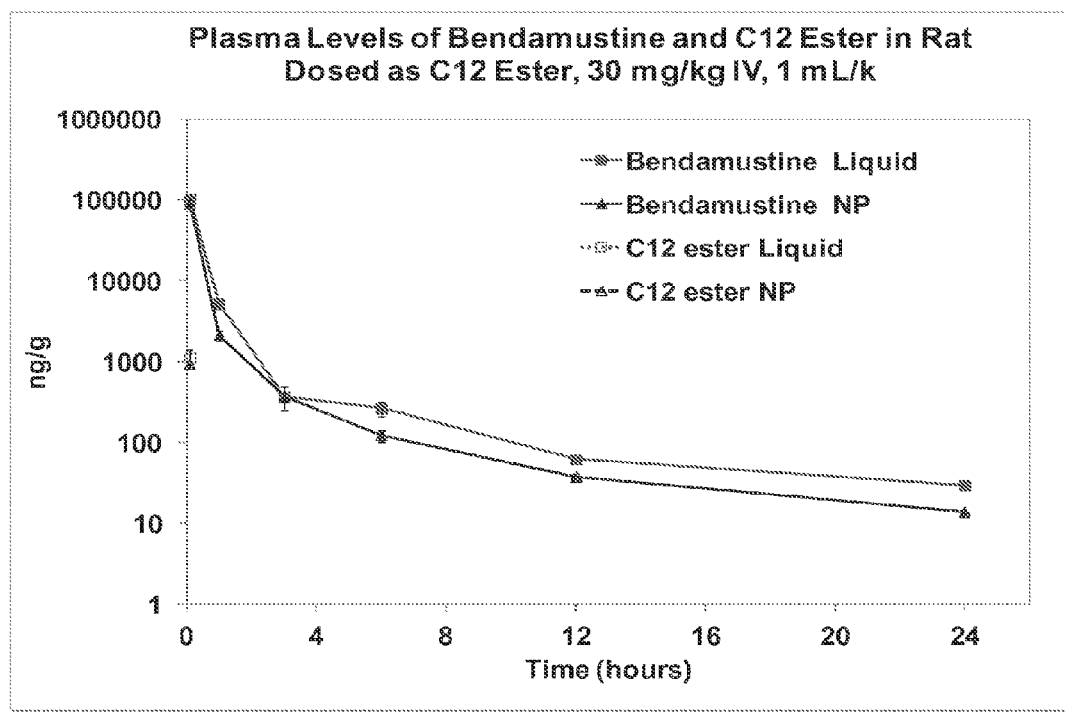
FIG. 8 depicts plasma levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 4 is also depicted in FIG. 8.

TABLE 5

| Blood | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 6.3 | ND | 5.7 | ND |
| $AUC_{0-t}$, ng * h/mL | 91549 | 4424 | 58021 | 951 |
| $AUC_{0-\infty}$, ng * h/mL | 91856 | ND | 58112 | ND |

Figure 9:
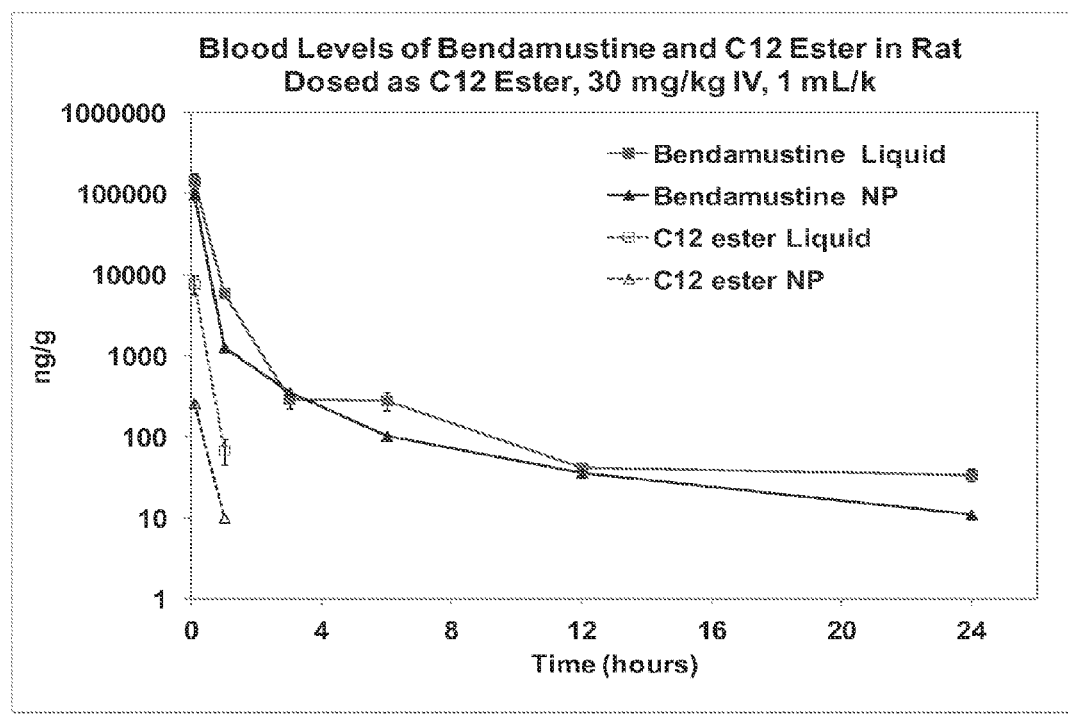
FIG. 9 depicts blood levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 5 is also depicted in FIG. 9.

TABLE 6

| Brain | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | ND | ND | ND | ND |
| $AUC_{0-t}$, ng * h/mL | 9284 | 299 | 1010 | 149 |
| $AUC_{0-\infty}$, ng * h/mL | ND | ND | ND | ND |

Figure 10:
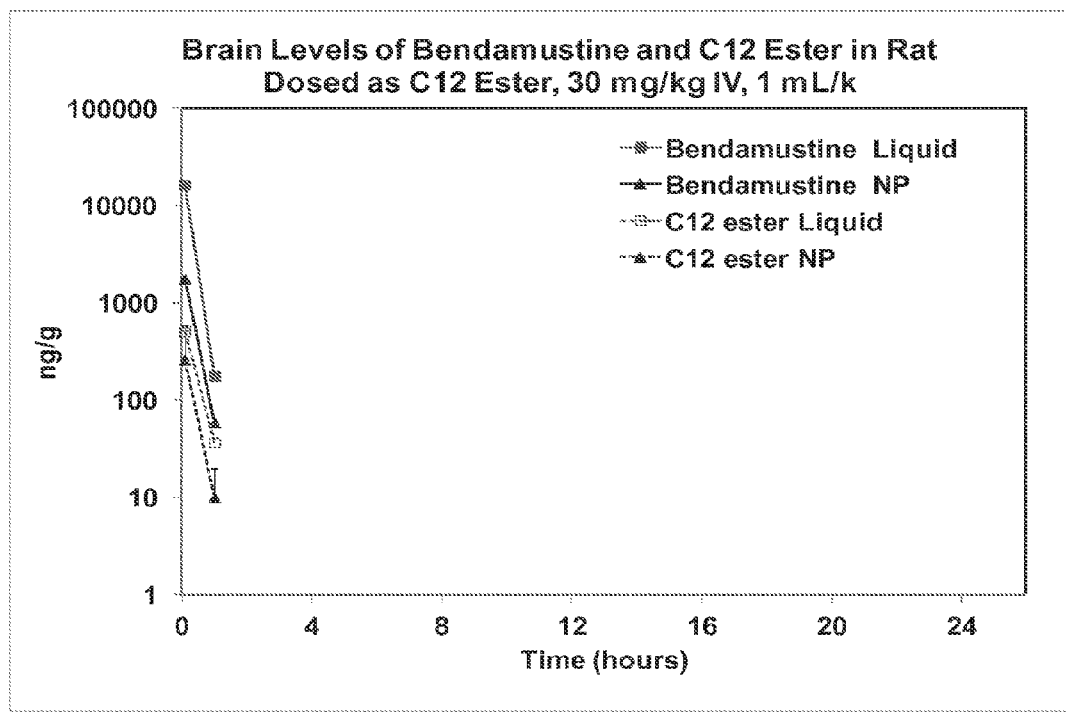
FIG. 10 depicts brain levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 6 is also depicted in FIG. 10.

TABLE 7

| Liver | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 4.2 | 0.8 | 2.6 | 4.5 |
| $AUC_{0-t}$, ng * h/mL | 13901 | 2564 | 43785 | 13355 |
| $AUC_{0-\infty}$, ng * h/mL | 14111 | 2586 | 44713 | 13586 |

Figure 11:
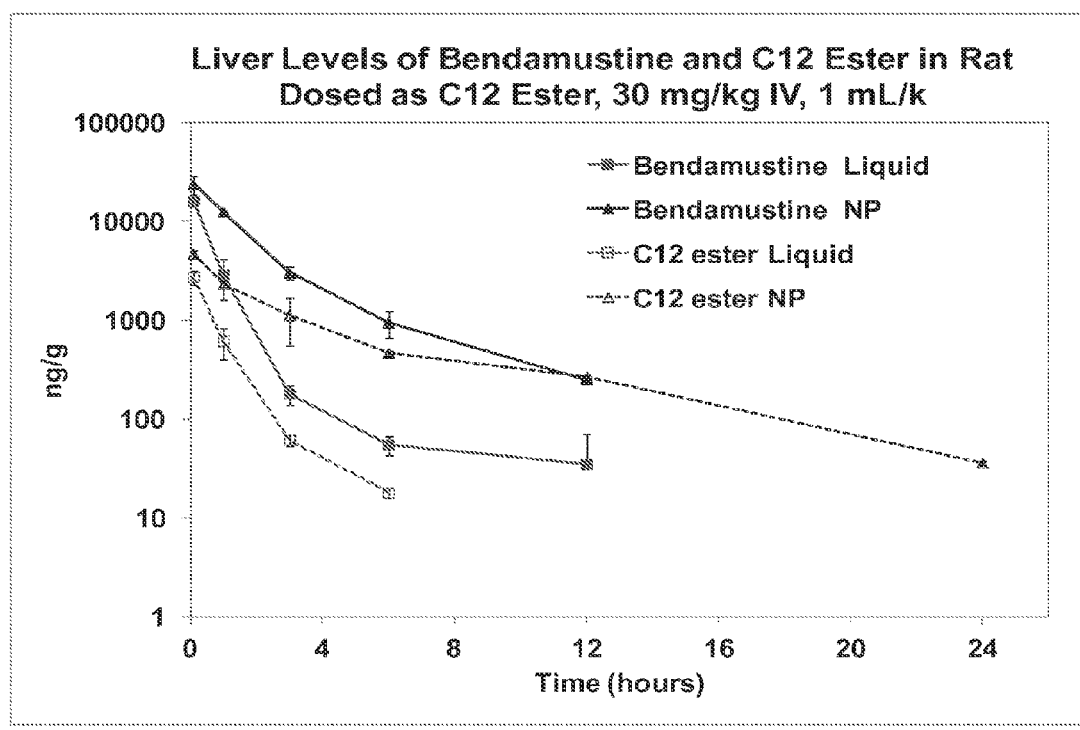
FIG. 11 depicts liver levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 7 is also depicted in FIG. 11.

TABLE 8

| Lung | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 2.0 | 7.6 | 5.1 | 8.5 |
| $AUC_{0-t}$, ng * h/mL | 22229 | 12619 | 15075 | 28327 |
| $AUC_{0-\infty}$, ng * h/mL | 22286 | 13246 | 15590 | 32297 |

Figure 12:
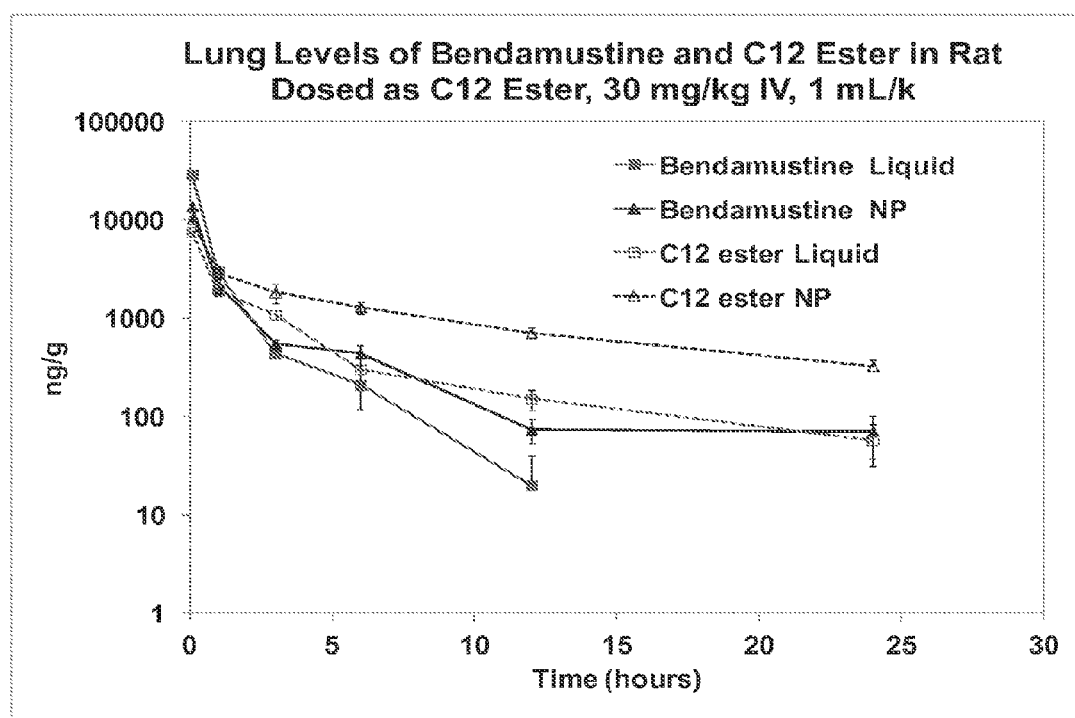
FIG. 12 depicts lung levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 8 is also depicted in FIG. 12.

TABLE 9

| Spleen | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 2.3 | 3.1 | 1.6 | 5.4 |
| $AUC_{0-t}$, ng * h/mL | 10201 | 25874 | 2598 | 13111 |
| $AUC_{0-\infty}$, ng * h/mL | 10362 | 25927 | 2735 | 13578 |

Figure 13:
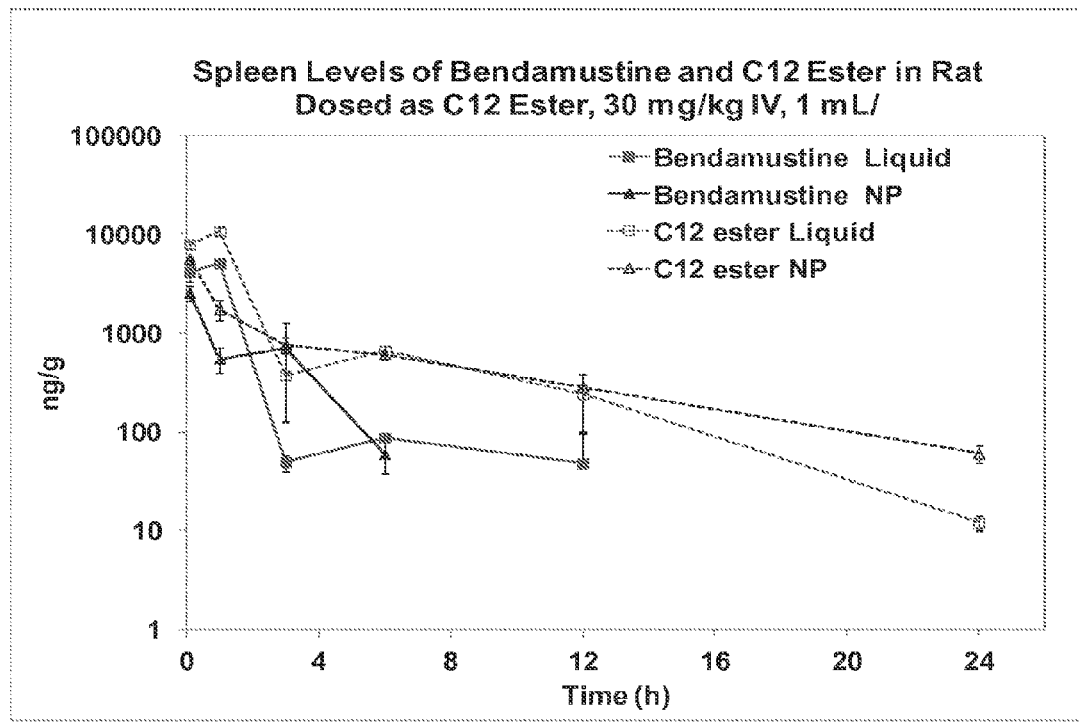
FIG. 13 depicts spleen levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 9 is also depicted in FIG. 13.

TABLE 10

| Kidney | Liquid Formulation | | Nanoparticle Formulation | |
|---|---|---|---|---|
| | Bendamustine | $C_{12}$ Ester | Bendamustine | $C_{12}$ Ester |
| $t_{1/2}$, h | 6.4 | 5.3 | 7.0 | 4.9 |
| $AUC_{0-t}$, ng * h/mL | 19489 | 2383 | 9665 | 1766 |
| $AUC_{0-\infty}$, ng * h/mL | 19966 | 2605 | 10725 | 1802 |

Figure 14:
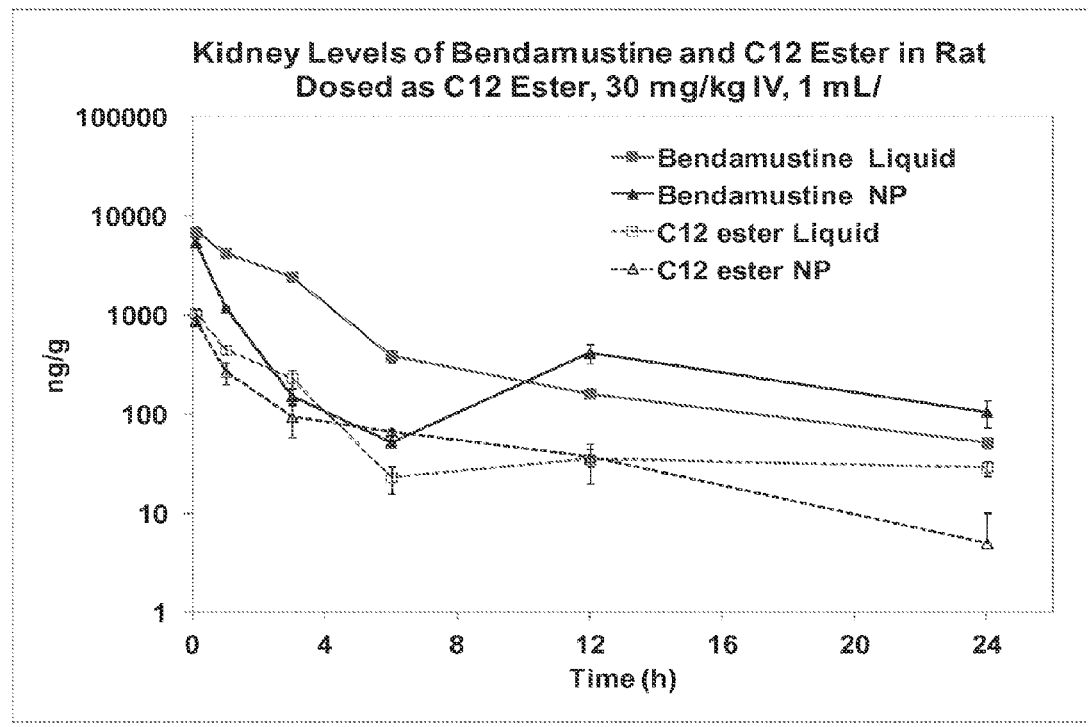
FIG. 14 depicts kidney levels of bendamustine and one embodiment of the invention, bendamustine $C_{12}$ ester (as liquid and nanoparticle formulations), after dosing rats at 30 mg/kg i.v., 1 mL/kg with bendamustine $C_{12}$ ester.

The data from Table 10 is also depicted in FIG. 14.

TABLE 11

Figure 15:
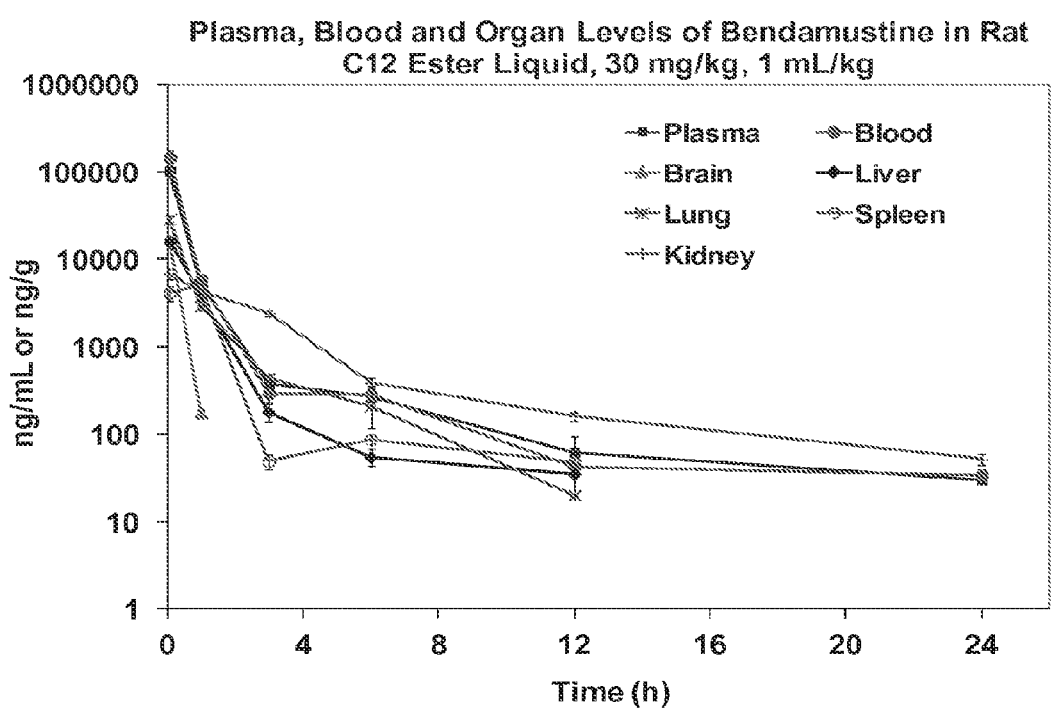
FIG. 15 depicts plasma, blood, and organ levels of bendamustine in rat after administration of one embodiment of the invention, bendamustine $C_{12}$ ester (as liquid formulation), after dosing rats at 30 mg/kg i.v., 1 mL/kg.

Plasma, Blood, and Organ Levels of Bendamustine in Rat After Administration of Bendamustine $C_{12}$ Ester Liquid Formulation, 30 mg/mL, 1 mL/kg FIG. 15

| | Plasma | Blood | Brain | Liver | Lung | Spleen | Kidney |
|---|---|---|---|---|---|---|---|
| $t_{1/2}$, h | 5.7 | 6.3 | ND | 4.2 | 2.0 | 2.3 | 6.4 |
| $AUC_{0-t}$, ng * h/mL | 66885 | 91549 | 9284 | 13901 | 22229 | 10201 | 19489 |
| $AUC_{0-\infty}$, ng * h/mL | 67131 | 91856 | ND | 14111 | 22286 | 10362 | 19966 |

The data from Table 11 is also depicted in FIG. 15.

TABLE 12

Figure 16:
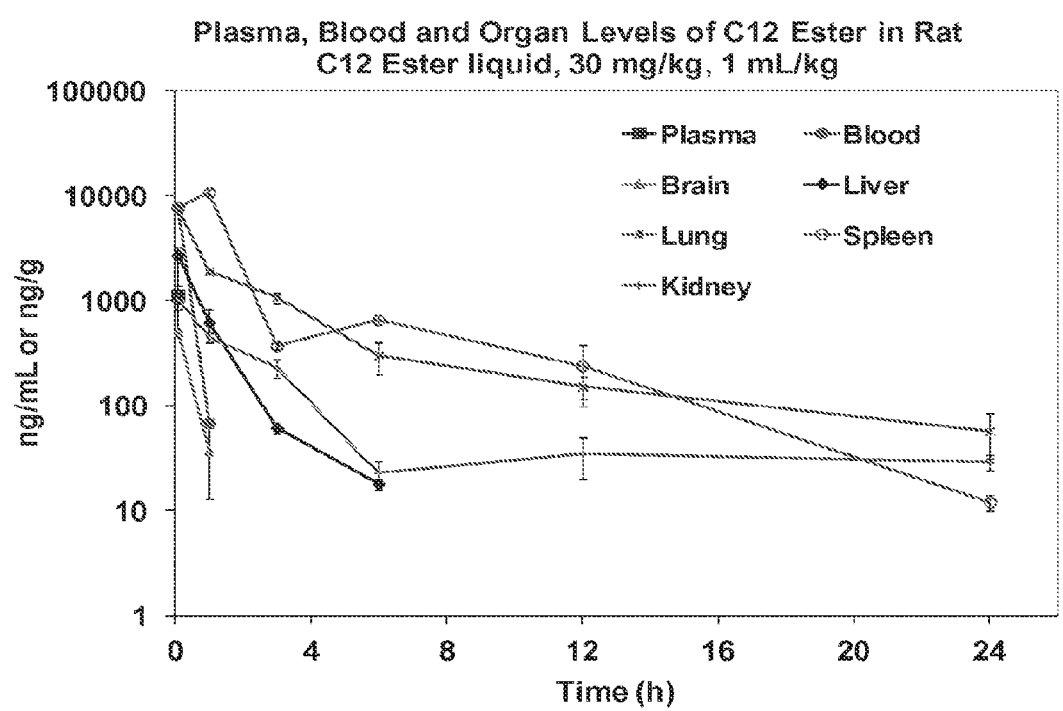
FIG. 16 depicts plasma, blood, and organ levels of one embodiment of the invention, bendamustine $C_{12}$ ester, in rat after dosing rats at 30 mg/kg i.v., 1 mL/kg with bendamustine $C_{12}$ ester (as liquid formulation).

Plasma, Blood, and Organ Levels of Bendamustine $C_{12}$ Ester After Administration of Bendamustine $C_{12}$ Ester Liquid Formulation, 30 mg/mL, 1 mL/kg FIG. 16

|  | Plasma | Blood | Brain | Liver | Lung | Spleen | Kidney |
|---|---|---|---|---|---|---|---|
| $t_{1/2}$, h | ND | ND | ND | 0.8 | 7.6 | 3.1 | 5.3 |
| $AUC_{0-t}$, ng * h/mL | ND | 4424 | 299 | 2564 | 12619 | 25874 | 2383 |
| $AUC_{0-\infty}$, ng * h/mL | ND | ND | ND | 2586 | 13246 | 25927 | 2605 |

The data from Table 12 is also depicted in FIG. 16.

TABLE 13

Figure 17:
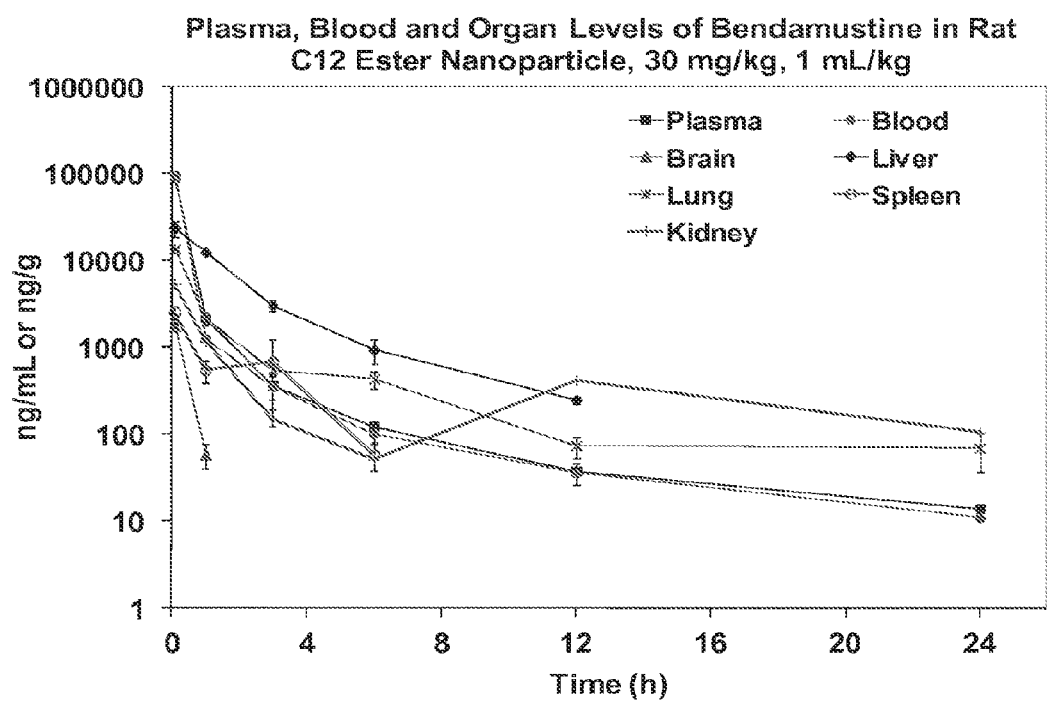
FIG. 17 depicts plasma, blood, and organ levels of bendamustine in rat after administration of one embodiment of the invention, bendamustine $C_{12}$ ester (as nanoparticle formulation), after dosing rats at 30 mg/kg i.v., 1 mL/kg.

Plasma, Blood, and Organ Levels of Bendamustine in Rat After Administration of Bendamustine $C_{12}$ Ester Nanoparticle Formulation, 30 mg/mL, 1 mL/kg FIG. 17

|  | Plasma | Blood | Brain | Liver | Lung | Spleen | Kidney |
|---|---|---|---|---|---|---|---|
| $t_{1/2}$, h | 6.0 | 5.7 | ND | 2.6 | 5.1 | 1.6 | 7.0 |
| $AUC_{0-t}$, ng * h/mL | 55296 | 58021 | 1010 | 43785 | 15075 | 2598 | 9665 |
| $AUC_{0-\infty}$, ng * h/mL | 55417 | 58112 | ND | 44713 | 15590 | 2735 | 10725 |

The data from Table 13 is also depicted in FIG. 17.

TABLE 14

Figure 18:
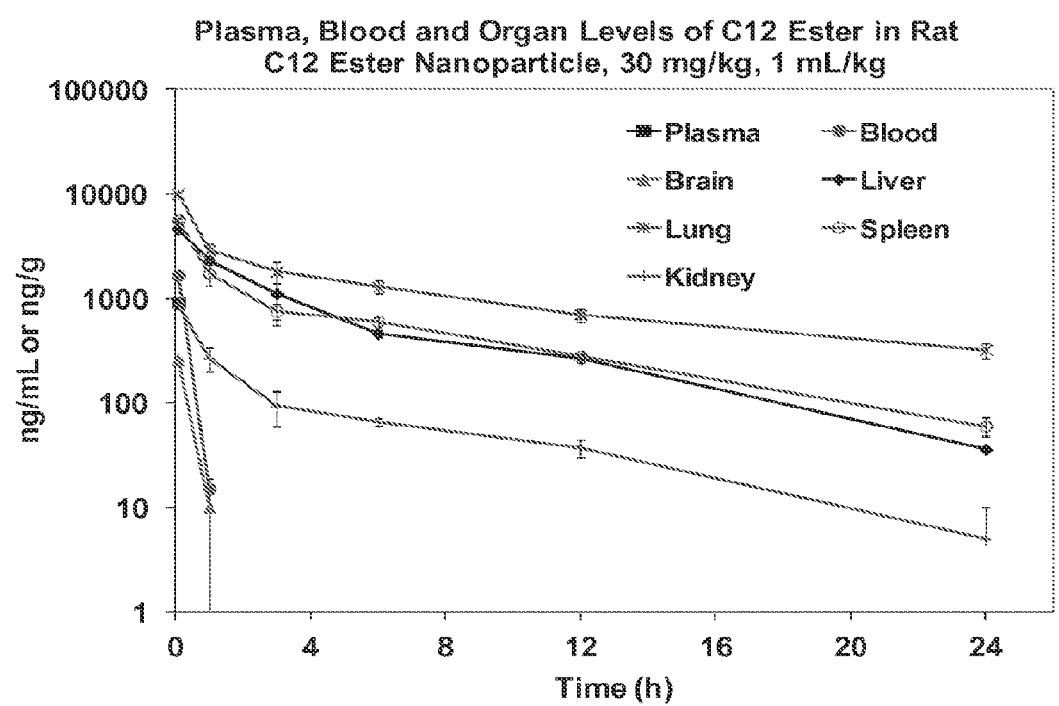
FIG. 18 depicts plasma, blood, and organ levels of one embodiment of the invention, bendamustine $C_{12}$ ester, in rat after dosing rats at 30 mg/kg i.v., 1 mL/kg with bendamustine $C_{12}$ ester (as nanoparticle formulation).

Plasma, Blood, and Organ Levels of Bendamustine $C_{12}$ Ester After Administration of Bendamustine $C_{12}$ Ester Nanoparticle Formulation, 30 mg/mL, 1 mL/kg FIG. 18

|  | Plasma | Blood | Brain | Liver | Lung | Spleen | Kidney |
|---|---|---|---|---|---|---|---|
| $t_{1/2}$, h | ND | ND | ND | 4.5 | 8.5 | 5.4 | 4.9 |
| $AUC_{0-t}$, ng * h/mL | ND | 951 | 149 | 13355 | 28327 | 13111 | 1766 |
| $AUC_{0-\infty}$, ng * h/mL | ND | ND | ND | 13586 | 32297 | 13578 | 1802 |

The data from Table 14 is also depicted in FIG. 18.

TABLE 15

Plasma Levels of Bendamustine in Rat After Dosing Bendamustine $C_{12}$ Ester Nanoparticles at 3 mg-eq/kg, i.v.: Comparison of Different Formulations FIG. 19

| Formulation | Treanda | HSA | HSA/PLGA | PLGA/PELA | HSA w/PEG |
|---|---|---|---|---|---|
| $t_{1/2}$, h | 0.16 ± 0.01 | 0.63 ± 0.09 | 0.41 ± 0.04 | 2.1 ± 0.3 | 1.6 ± 0.3 |
| $AUC_{0-t}$, ng * h/mL | 1609 ± 77 | 773 ± 58 | 1120 ± 113 | 856 ± 93 | 1194 ± 186 |
| $AUC_{0-\infty}$, ng * h/mL | 1631 ± 81 | 781 ± 58 | 1132 ± 115 | 959 ± 92 | 1250 ± 203 |
| Vd, L/kg | 0.42 ± 0.04 | 3.6 ± 0.7 | 1.6 ± 0.2 | 10.0 ± 2.2 | 6.1 ± 1.8 |
| CL, mL/min/kg | 31 ± 2 | 65 ± 5 | 46 ± 4 | 54 ± 5 | 44 ± 7 |

Mean ± SD, n = 4    Bendamustine $C_{12}$ Ester Nanoparticles

Figure 5:
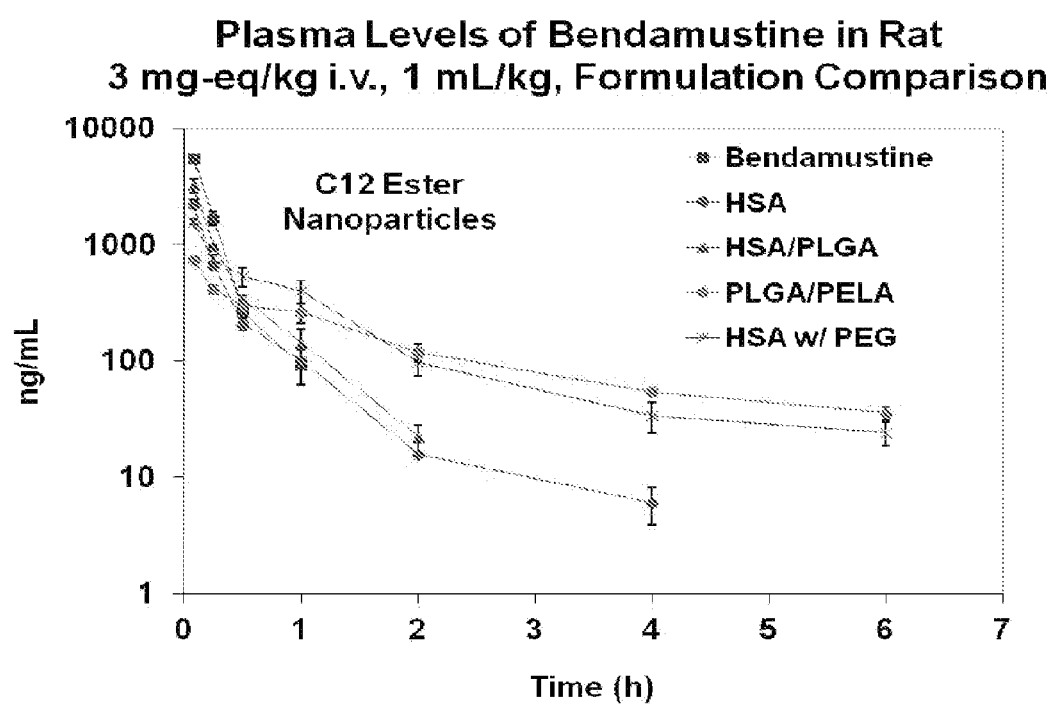
FIG. 5 depicts plasma levels of bendamustine in rats after dosing one embodiment of the invention in rats using different formulations.

The data from Table 15 is also depicted in FIG. 5.

TABLE 16

Plasma Levels of Bendamustine $C_{12}$ Ester in Rat After Dosing Bendamustine $C_{12}$ Ester Nanoparticles at 3 mg-eq/kg, i.v.: Comparison of Different Formulations FIG. 20

| Formulation | HSA | HSA/PLGA | PLGA/PELA | HSA w/PEG |
|---|---|---|---|---|
| $t_{1/2}$, h | ND | 0.12 ± 0.01 | 2.3 ± 0.0 | 0.20 ± 0.01 |
| $AUC_{0-t}$, ng * h/mL | 21 ± 2 | 18 ± 5 | 17 ± 3 | 55 ± 4 |
| $AUC_{0-\infty}$, ng * h/mL | ND | 21 ± 7 | 36 ± 5 | 56 ± 4 |
| Vd, L/kg | ND | 47 ± 15 | 428 ± 59 | 23.3 ± 2.5 |
| CL, mL/min/kg | ND | 4194 ± 1071 | 2109 ± 252 | 1335 ± 99 |

Mean ± SD, n = 4

Figure 6:
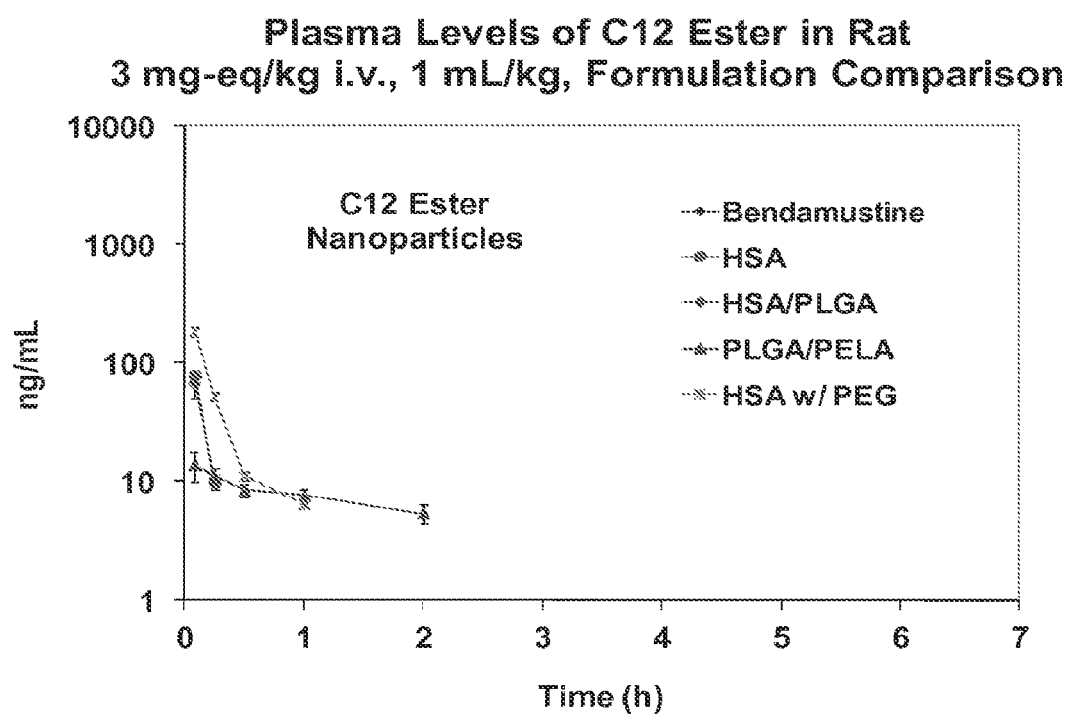
FIG. 6 depicts plasma levels of one embodiment of the invention in rats after dosing that embodiment in rats using different formulations.

The data from Table 16 is also depicted in FIG. 6.

TABLE 17

Plasma Levels of Bendamustine $C_{16}$ Ester, Cyclohexyl Ester, and 5-Decanyl Ester in Rat After Dosing Solution Formulations at 3 mg-eq/kg i.v.

| Plasma | Bendamustine Ester C16 bendamustine ester | | Bendamustine Ester 5-decanyl ester | | Bendamustine Ester Cy-hexyl bendamustine ester | |
|---|---|---|---|---|---|---|
| $t_{1/2}$, h | 0.46 | 0.28 | 0.16 | | 0.20 | |
| $AUC_{0-t}$, ng * h/mL | 505 | 1208 | 633 | | 504 | |
| $AUC_{0-\infty}$, ng * h/mL | 617 | 1214 | 642 | All < MQL | 517 | All < MQL |
| Vd, L/kg | 3.3 | 1.0 | 1.1 | | 1.6 | |
| CL, mL/min/kg | 82 | 41 | 78 | | 96 | |
| | 1.85% solvent | | 1.6% solvent | | 1.4% solvent | |
| Mean, n = 3 | Diluted into saline from 1/1/1 DMA/PG/Solutol | | | | | |

Another embodiment of the invention, bendamustine $C_{14}$ ester was formulated into a nanoparticle intravenous formulation according to the methods described above and administered to CD-1 mice. The amount of bendamustine (BM1) and bendamustine $C_{14}$ ester was determined in the mice plasma. The results of these experiments are summarized in Table 18.

TABLE 18

| | Plasma | | | | | |
|---|---|---|---|---|---|---|
| | BM1 30 mg-eq/kg | $C_{14}$ Ester 30 mg-eq/kg | BM1 55 mg-eq/kg | $C_{14}$ Ester 55 mg-eq/kg | BM1 80 mg-eq/kg | $C_{14}$ Ester 80 mg-eq/kg |
| $t_{1/2}$, h | 1.17 | 1.52 | 0.92 | 0.98 | 0.95 | 1.09 |
| $AUC_{0-6}$, ng * h/mL | 4507 | 31693 | 4152 | 48934 | 6007 | 46335 |
| $AUC_{0-\infty}$, ng * h/mL | 4524 | 31741 | 4188 | 49020 | 6068 | 46485 |
| Vd, L/kg | ND | 3.2 | ND | 2.5 | ND | 5.2 |
| CL, mL/min/kg | ND | 24 | ND | 29 | ND | 56 |
| Mean, n = 3 | | | Albumin Nanoparticle | | | |

Figure 19:
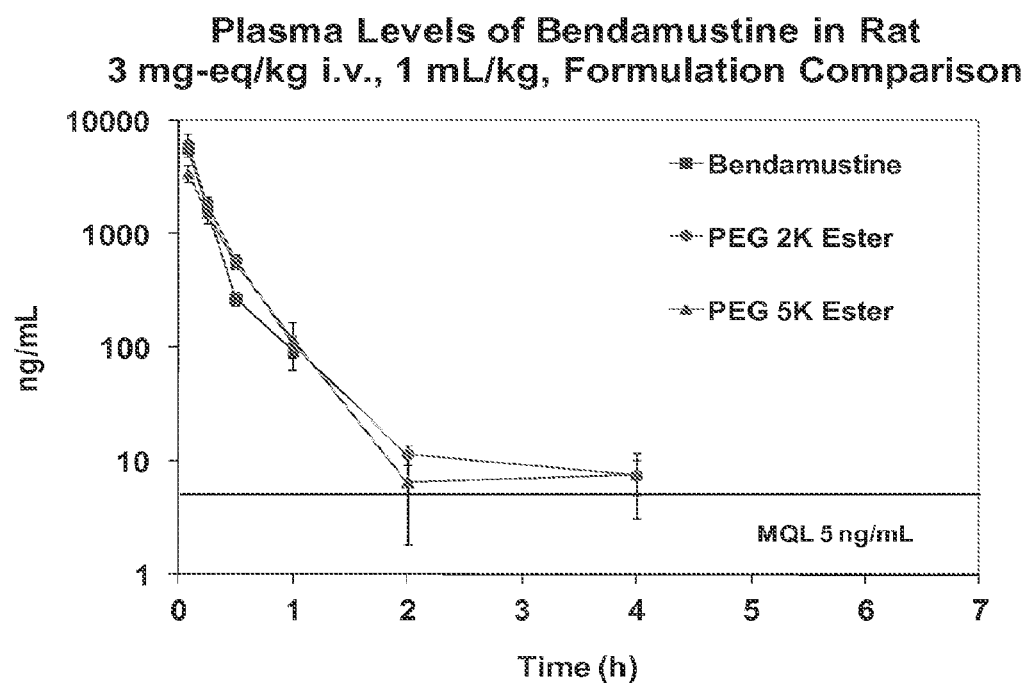
FIG. 19 depicts plasma levels of bendamustine in rat after administration of embodiments of the invention, bendamustine PEG-2000 ester and bendamustine PEG-5000 ester, after dosing rats at 3 mg-eq/kg i.v., 1 mL/kg. Comparison is with TREANDA.

PEG-ylated esters of bendamustine were also tested. Data for PEG-2000 and PEG-5000 esters of bendamustine is depicted in Tables 19 and 20 below. This data is also depicted in FIG. 19.

TABLE 19

Plasma Levels of Bendamustine in Rat Dased as Bendamustine PEG-2000 Ester, 3 mg-eq/kg i.v., 1 mL/kg

| Bendamustine | Rat 1 | Rat 2 | Rat 3 | Rat 4 | Mean | st. dev. | sem |
|---|---|---|---|---|---|---|---|
| $t_{1/2}$, h | 0.46 | 0.23 | 0.50 | 0.22 | 0.36 | 0.15 | 0.07 |
| $AUC_{0-6}$, ng * h/mL | 2100 | 2866 | 1494 | 1379 | 1960 | 682 | 341 |
| $AUC_{0-\infty}$, ng * h/mL | 2109 | 2868 | 1506 | 1382 | 1966 | 680 | 340 |
| Vd, L/kg | 0.95 | 0.35 | 1.46 | 0.70 | 0.87 | 0.46 | 0.23 |
| CL, mL/min/kg | 24 | 17 | 33 | 36 | 28 | 9 | 4 |
| bendamustine PEG-2000 ester | | | 3 mg-eq/kg, 1 mL/kg | | | | |

TABLE 20

Plasma Levels of Bendamustine in Rat Dased as Bendamustine PEG-5000 Ester, 3 mg-eq/kg i.v., 1 mL/kg

| Bendamustine | Rat 1 | Rat 2 | Rat 3 | Rat 4 | Mean | st. dev. | sem |
|---|---|---|---|---|---|---|---|
| $t_{1/2}$, h | 0.16 | 0.48 | 0.47 | 0.48 | 0.40 | 0.16 | 0.08 |
| $AUC_{0-6}$, ng * h/mL | 808 | 1735 | 1572 | 1050 | 1291 | 435 | 217 |
| $AUC_{0-\infty}$, ng * h/mL | 817 | 1741 | 1579 | 1058 | 1299 | 434 | 217 |

TABLE 20-continued

Plasma Levels of Bendamustine in Rat Dased as
Bendamustine PEG-5000 Ester, 3 mg-eq/kg i.v., 1 mL/kg

| Bendamustine | Rat 1 | Rat 2 | Rat 3 | Rat 4 | Mean | st. dev. | sem |
|---|---|---|---|---|---|---|---|
| Vd, L/kg | 0.84 | 1.19 | 1.29 | 1.99 | 1.32 | 0.48 | 0.24 |
| CL, mL/min/kg | 61 | 29 | 32 | 48 | 42 | 15 | 8 |
| bendamustine PEG-5000 ester | | | 3 mg-eq/kg, 1 mL/kg | | | | |

Analysis of the In-Vitro Stability of Bendamustine Esters

Tumor S9 Preparation:

Charles River Labs athymic nude mice bearing breast (MB-231) or non-small-cell lung cancers (H460) were sacrificed. Tumors were immediately removed and rinsed with ice-cold 1.15% KCl. The tumors were weighed, cut and minced. Minced tissues were mixed with 4x (v/w) ice-cold SET buffer (250 mM sucrose, 5.4 mM $Na_2EDTA$ and 20 mM Tris, pH 7.4) and homogenized with tissue homogenizers. Homogenates were transferred into clean polycarbonate ultracentrifuge tubes and spun at 10,000 g at 4° C. for 20 min. Lipid at the top of the ultracentrifuge tubes was removed with cotton swabs, and the supernatant (S9) aliquots were stored in a −80° C. freezer.

In Vitro Incubation:

Incubation mixture containing 50 mM phosphate buffer (pH 7.4), an NADPH-(reduced nicotinamide adenosine diphosphate) regenerating system and 1 mg/mL tumor S9 were pre-warmed in a 37° C. water bath. Reactions were initiated by adding 1 μL of bendamustine C6, C8, C12 or C14 ester into separate incubation mixtures to obtain final concentrations of each bendamustine ester of 10 μM. At designed time points, 100-μL aliquots of the incubation mixtures were removed and mixed with 400 μL of stop solution (4 or 8 μM tiagabine [IS] in a solution of 0.1% formic acid/acetonitrile). All samples were vortex-mixed and placed on ice for at least 10 min and then the protein was precipitated by centrifuging in an Eppendorf 5417R centrifuge at 14000 rpm×8 min. The supernatant was transferred into HPLC vials and 10 μL was injected for analysis using high performance liquid chromatography with tandem mass spectrometric detection.

LC-MS/MS Method:

The LC-MS/MS system consisted of a Shimadzu HPLC and a Sciex API 4000 MS. The chromatography was performed on a Phenomenex 00B-4448-B0, Luna PFP(2) column (50×2 mm, 5 μm particle size). The total mobile phase flow rate was 0.5 mL/min. The gradient began at 70% mobile phase A (0.1% aqueous trifluoroacetic acid) and 30% mobile phase B (100% acetonitrile). The proportion of mobile phase B was then linearly increased to 95% within 0.5 min and was maintained at that ratio for 1.3 min, re-equilibrating to initial conditions within 1 min. The mass spectrometer was tuned to the respective optimal conditions for each bendamustine ester, monitoring transitions of 442.2/340.1 (C6), 470.2/340.1 (C8), 526.3/340.1 (C12) and 554.3/340.1 (C14).

Figure 3:
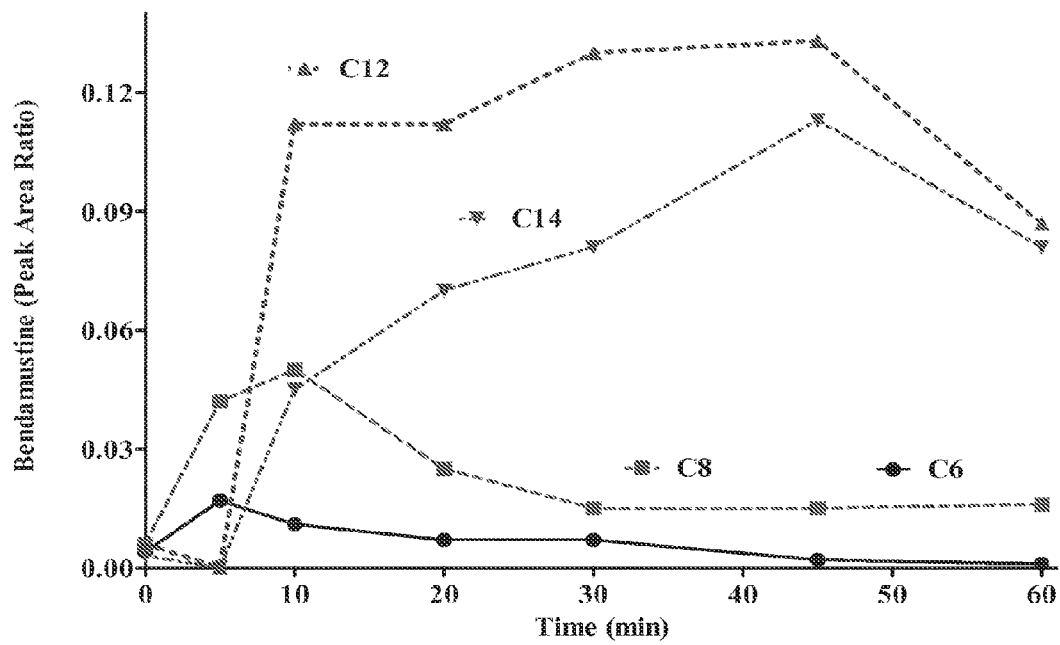
FIG. 3 depicts the amount of bendamustine observed over time after treating MDA-MB-231 breast tumor S9 with certain embodiments of the invention.
Figure 4:
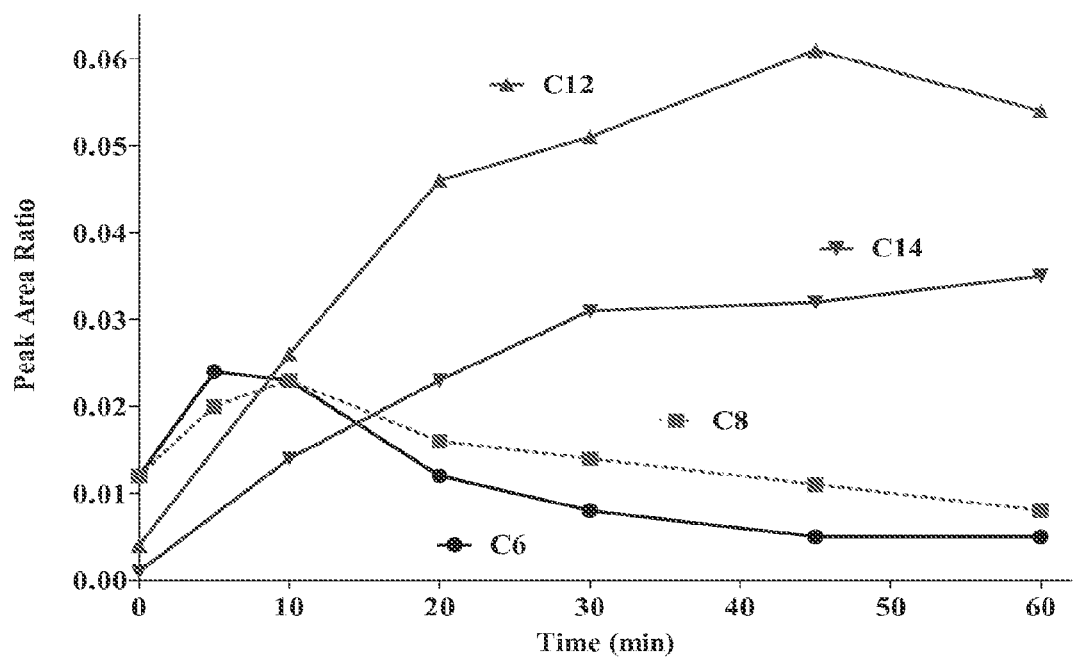
FIG. 4 depicts the amount of bendamustine observed over time after treating H460 non small cell lung tumor S9 with certain embodiments of the invention.

Data from the in-vitro stability studies is set forth in FIGS. 3 and 4.

Electron Microscopy Experimentals

Sample Preparation for c-TEM Study:

Sample was solubilized by adding 7.8 mL of water for injection (WFI) to the sample and mixed by inverting by hand. Sample dissolved quickly, ~2-5 minutes, with no visible undissolved particles in the solution. The sample was preserved in vitrified ice supported by carbon coated holey carbon films on 400 mesh copper grids. The sample was prepared by applying a 3 μL drop of undiluted sample solution to a cleaned grid, blotting away with filter paper and immediately proceeding with vitrification in liquid ethane. Grids were stored under liquid Nitrogen until transferred to the electron microscope for imaging.

c-TEM Imaging Parameters:

Electron microscopy was performed using an FEI Tecnai T12 electron microscope, operating at 120 KeV equipped with an FEI Eagle 4K×4K CCD camera. The grid was transferred into the electron microscope using a cryostage that maintains grids at a temperature below −170 C. Images of the grid were acquired at multiple scales to assess the overall distribution of the specimen. After identifying potentially suitable target areas for imaging at lower magnifications, high magnification images were acquired at nominal magnifications of 52,000× (0.21 nm/pixel), and 21,000× (0.50 nm/pixel). The images were acquired at a nominal underfocus of −4 μm (52,000×) and −5 μm (21,000×) and electron doses of ~10-15 e/Å2.

Figure 7:
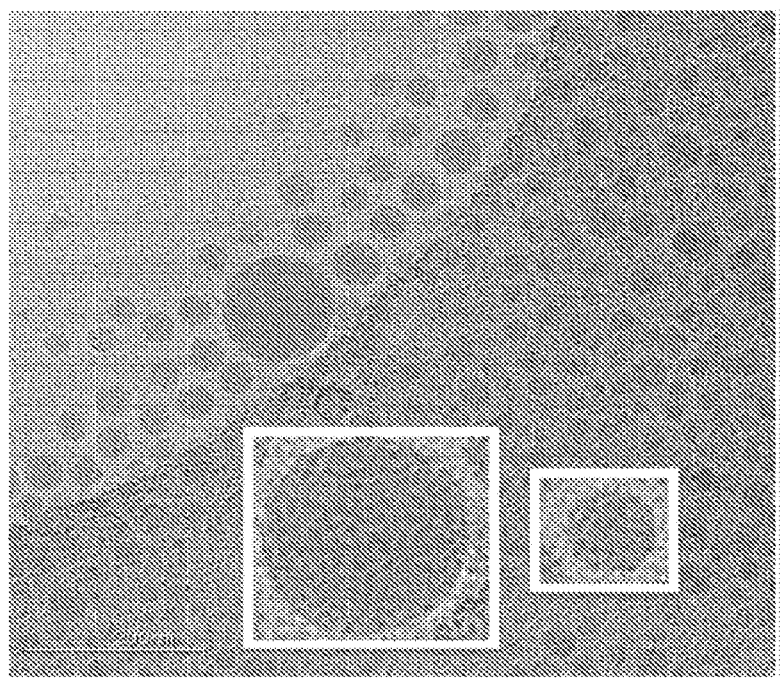
FIG. 7 depicts Cryo-TEM images of nanoparticles of one embodiment of the invention, bendamustine $C_{14}$ ester.

Results of the electron microscopy experiments is depicted in FIG. 7.

Cross-Linking Experiments with HSA Nanoparticles Formulation of Bendamustine Esters Circulation times of bendamustine and bendamustine esters of the invention can be extended using HSA-based nanoparticle formulation wherein the protein moieties are covalently cross-linked after the nanoparticle structures are formed. See, e.g., K. Langer et al. *International Journal of Pharmaceutics* 347 (2008) 109-117. This would provide more structure to the surface coating and would prevent a rapid release of the nanoparticle contents. This could also provide "stealth" protection of the nanoparticle by introducing a PEG group to the cross-linking agent. Effective encapsulation and hardening of the HSA nanoparticle was demonstrated using the commercially available dialdehyde, glutaraldehyde. Introduction of an appropriately-sized PEG moiety could be added using, for example, the trifunctional PEG cross-linking agent prepared as shown below:

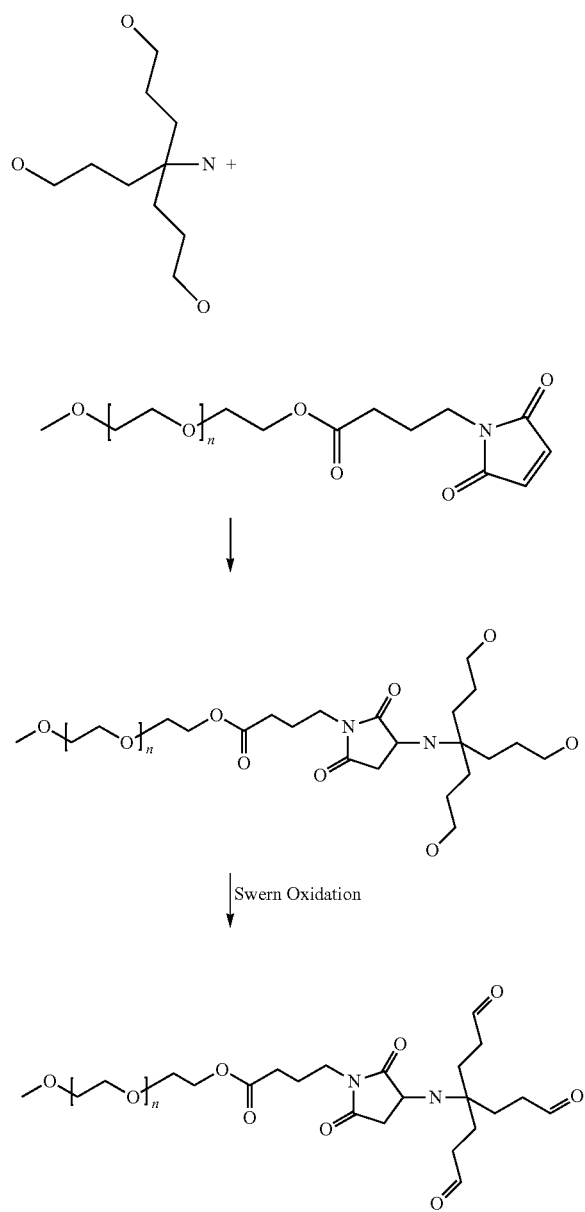

Procedure:

HSA nanoparticles were diluted with DI water to a concentration of 1.5 mg/mL C14 ester of bendamustine, which corresponds to a 6 mg/mL concentration of HSA. The resulting suspension of nanoparticles was then aliquoted in 1 mL portion into five glass vials outfitted with a magnetic stir bar. The appropriate amount of a 50% glutaraldehyde solution was added and each vial was capped and stirred at room temperature over-night. Each sample was then diluted 1 to 10 into N-methylpyrrolidone (NMP) and the sample spun for ~2 minutes using a micro-centrifuge to remove HSA and cross-linked HSA nanoparticles. The supernatant was then analyzed by HPLC and the concentration (peak area) of the C14 ester of bendamustine was determined to confirm particle encapsulation. The table below shows the concentration of un-encapsulated C14 ester of bendamustine as a function of the μL of gluturaldehyde:

| μL of glutaraldehyde | HPLC Peak Area |
|---|---|
| 0 | 4882.02 |
| 2 | 4788.99 |
| 5 | 4778.11 |
| 10 | 4714.02 |
| 20 | 29.55 |

The data shows that the addition of glutaraldehyde at a ratio of 3.33 μL/mg of HSA was suitable to result in a system of cross-linked, bendamustine ester-containing nanoparticles.

In Vivo Multiple Myeloma Model
Materials and Methods
RPMI 8226 (Human Plasmacytoma, Myeloma B Cells) ATCC #CCL-155;
ECM Gel (Matrigel), Sigma-Aldrich, Cat #E1270, 5 ml
RPMI (Beit Haemek, Lot: 1110235)
Velcade® (Bortezomib) 3.5 mg lyophilized in vial, Lot# BIZSC00
Bendamustine (Lot #TD-D0815, API Lot #00039P0012)
Bendamustine C12 ester nanoparticles (C12NP), Lot #2861-242-22, 17.6 mg/vial
Sodium chloride
Water for injections (DEMO S.A.)
Test Animals
80 CB.17 SCID female mice, 4-6 weeks old, 16-20 grams, obtained from Harlan animal breeding center
Cells Preparation
Cells (originated from ATCC) were cultured on RPMI medium. Cell suspension was centrifuged and resuspended in 50% Matrigel/HBSS to a final concentration of $7\times10^7$ cells/ml. The suspension was implanted s.c. in the right flank of the anesthetized mouse at a volume of 100 μl.
Compounds Preparation
VELCADE® was prepared once a week. Seven ml saline were added to the original vial containing 3.5 mg powder resulting in 0.5 mg/ml. Three ml of this solution were added to 27 ml saline to receive 0.05 mg/ml concentration.
bendamustine preparation: 13.5 mg was dissolved in 3.6 ml of 1:1 mixture of 0.9% saline/5% mannitol just before the treatment. 1.05 ml of this solution was added to 0.95 ml diluent for 2 mg/ml solution.
C12NP preparation: 3.1 ml SWFI was added into sample vial containing 17.62 mg just before the treatment. 1.05 ml of this solution was added to 0.95 ml diluent for 2 mg/ml solution.
Experimental Design
Mice were implanted subcutaneously, with $7\times10^6$ RPMI 8226 cells/mouse (in 50% Martigel/HBSS) on Day 0. On day 21, mice were sorted by the optimal average tumor volume (~150 mm$^3$) and were allocated into eight groups of 9 mice each.

| Gr. | N | Agent | Route | Dose & schedule |
|---|---|---|---|---|
| 1 | 9 | WFI | iv | Days 1 & 2 |
| 2 | 9 | Velcade | iv | 0.5 mg/kg biweekly |
| 3 | 9 | Bendamustine | iv | 20 mg/kg on days 1&2 |
| 4 | 9 | Bendamustine | iv | 37.5 mg/kg on days 1&2 |
| 5 | 9 | C12NP | iv | 20 mg/kg on days 1&2 |
| 6 | 9 | C12NP | iv | 37.5 mg/kg on days 1&2 |

It should be noted that the nature of SCID mice (i.e., severely immune-compromised) make them more fragile/sensitive animals, and they are therefore less able to tolerate the doses of C12NP used in NUDE mice (which are comparatively less immune-compromised). Specifically, dosing SCID mice at 100 mg/kg and 70 mg/kg revealed unacceptable tolerance issues (i.e., more than 20% body weight loss)(data not shown). It is believed that this (tolerance difference between nude vs. SCID) is a strain-related phenomenon. As such, the study proceeding using doses of 37.5 mg/kg and 20 mg/kg of C12NP.

Statistical Analysis

Tumor volume was calculated as follows:

$$\pi \times \left(\frac{\text{width}}{2}\right)^2 \times \text{length}.$$

The analysis of weight gain and tumor volume progression was made using one-way ANOVA followed by Tukey post-hoc comparisons.

Results

Figure 23:
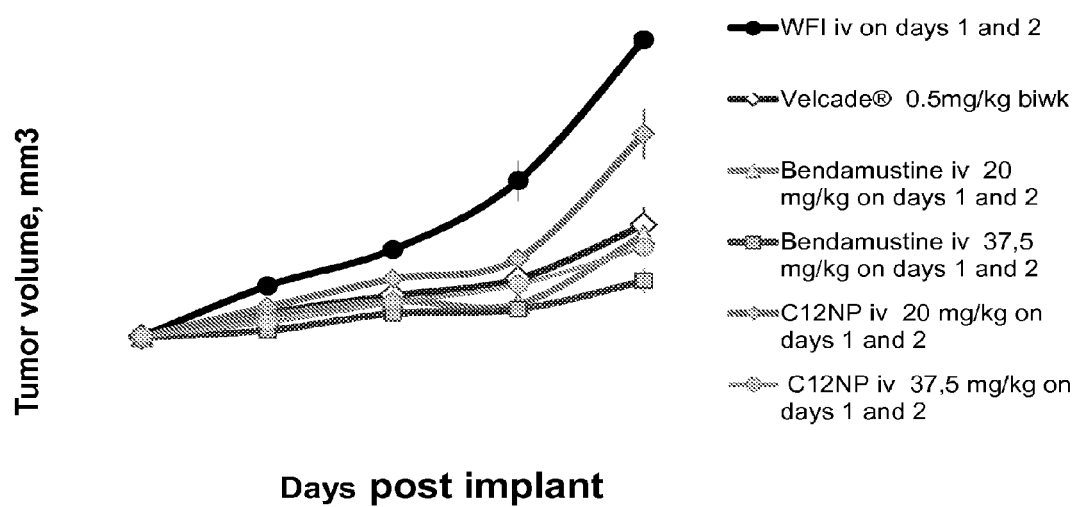
FIG. 23 depicts tumor volumes following administration of VELCADE®, bendamustine, and bendamustine C12 ester nanoparticles.
Figure 24:
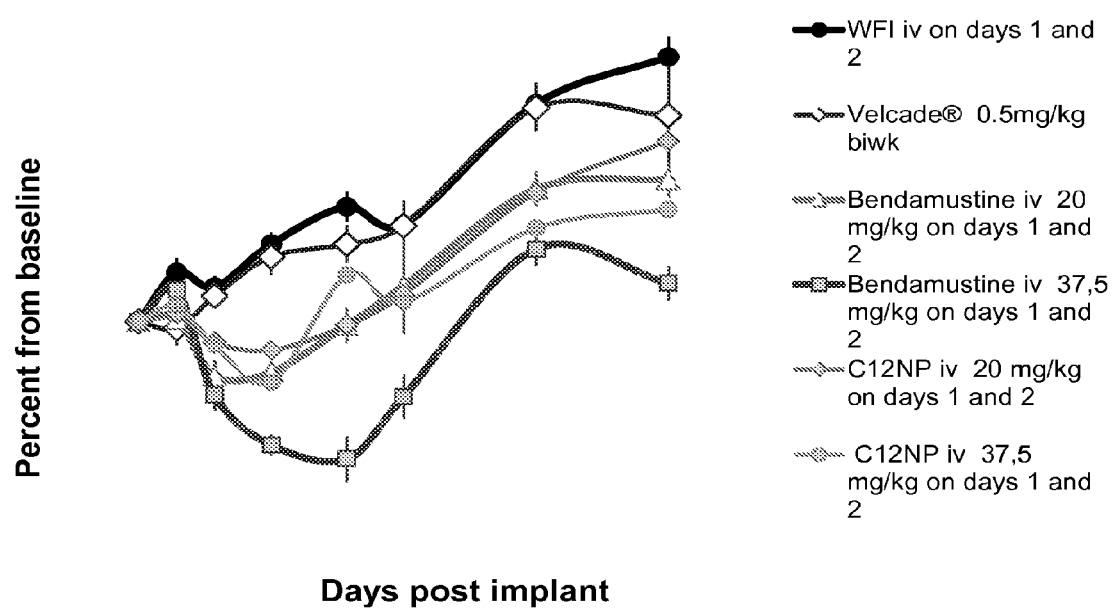
FIG. 24 depicts body weight measurements following administration of VELCADE®, bendamustine, and bendamustine C12 ester nanoparticles.

The treatment responses are summarized in FIGS. 23 and 24. All the treatments except C12NP 20 mg/kg significantly inhibited tumor growth compared to control group (see data in Table 21). At 37.5 mg/kg, the efficacy of Bendamustine and C12NP were similar, with 81% and 70% inhibition of tumor growth. However, as can be seen in FIG. 24, the tolerability of C12NP was better than Bendamustine as measured by less weight loss in animals treated with C12NP.

TABLE 21

Summary of Results (day 46)

| Compound | Regimen | Δ mean tumor volume, (mean ± se) | % TGI | No. of PR | No. of CR | Max BW (mean) reduction | No. of TRD | No. og nTRD |
|---|---|---|---|---|---|---|---|---|
| 1. Vehicle | WFI iv on days 1 and 2 | 597 ± 71 | | | | | | |
| 2. Velcade ® 0.5 mg/kg | i.v. biwk | 226 ± 35 | 62*** | 0 | 0 | −0.4% day 20 | 0 | 0 |
| 3. Bendamustine 20 mg/kg | iv on days 1 and 2 | 205 ± 44 | 66*** | 0 | 0 | −2.7% day 22 | 0 | 0 |
| 4. Bendamustine 37.5 mg/kg | iv on days 1 and 2 | 113 ± 23 | 81*** | 0 | 0 | −6.2% day 25 | 0 | 0 |
| 5. C12NP 20 mg/kg | iv on days 1 and 2 | 408 ± 49 | 32 | 0 | 0 | −1.5% day 25 | 0 | 0 |
| 6. C12NP 37.5 mg/kg | iv on days 1 and 2 | 180 ± 31 | 70*** | 0 | 0 | −3.1% day 25 | 0 | 0 |

***p < 0.001 (one-way Anova, Tukey post-hoc test)

What is claimed:

1. A method of treating cancer in a patient comprising administering to said patient a pharmaceutical composition, wherein said pharmaceutical composition comprises:

(a) a compound of formula (I)

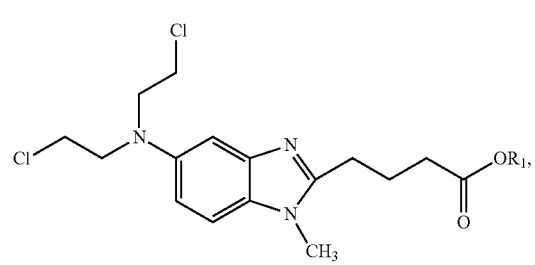

(I)

wherein $R_1$ is $C_8$-$C_{24}$ alkyl, or a pharmaceutically acceptable salt thereof; and (b) a means for increasing the circulation time of the compound of formula (I), or a pharmaceutically acceptable salt thereof, in an aqueous environment.

2. The method according to claim 1, wherein said cancer is in the form of a solid tumor or a liquid tumor.

3. The method according to claim 2, wherein said cancer is in the form of a solid tumor.

4. The method according to claim 3, wherein said cancer is sarcoma, bladder cancer, cervical cancer, testicular cancer, melanoma, glioblastoma, colon cancer, head and neck cancer, ovarian cancer, prostate cancer, breast cancer, or lung cancer.

5. The method according to claim 1, wherein said cancer is in the form of a liquid tumor.

6. The method according to claim 5, wherein said cancer is lymphocytic leukemia, Hodgkin's disease, non-Hodgkin's lymphoma, multiple myeloma, or acute lymphocytic leukemia.

7. The method according to claim 1, wherein in the compound of formula (I) $R_1$ is $C_{10}$-$C_{24}$ alkyl.

8. The method according to claim 1, wherein in the compound of formula (I) $R_1$ is $C_{12}$-$C_{24}$ alkyl.

9. The method according to claim 1, wherein in the compound of formula (I) $R_1$ is $C_{14}$-$C_{24}$ alkyl.

10. The method according to claim 1, wherein in the compound of formula (I) $R_1$ is $C_{10}$ alkyl.

11. The method according to claim 1, wherein in the compound of formula (I) $R_1$ is $C_{12}$ alkyl.

12. The method according to claim 1, wherein in the compound of formula (I) $R_1$ is $C_{14}$ alkyl.

13. The method according to claim 1, wherein in the compound of formula (I) $R_1$ is $C_{15}$ alkyl.

14. The method according to claim 1, wherein in the compound of formula (I) $R_1$ is $C_{16}$ alkyl.

15. A method of treating cancer in a patient comprising administering to said patient a pharmaceutical composition, wherein said pharmaceutical composition comprises:

(a) a compound of the formula

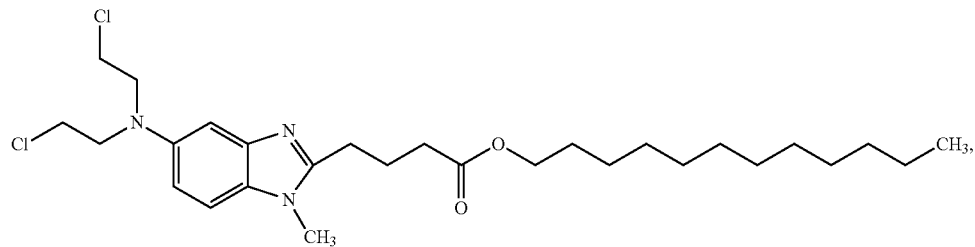 [SMILES: CCCCCCCCCCCCOC(=O)CCCc1nc2cc(N(CCCl)CCCl)ccc2n1C]

or a pharmaceutically acceptable salt thereof; and (b) a means for increasing the circulation time of the compound, or a pharmaceutically acceptable salt thereof, in an aqueous environment.

16. The method according to claim 15, wherein said cancer is in the form of a solid tumor or a liquid tumor.

17. The method according to claim 16, wherein said cancer is in the form of a solid tumor.

18. The method according to claim 17, wherein said cancer is sarcoma, bladder cancer, cervical cancer, testicular cancer, melanoma, glioblastoma, colon cancer, head and neck cancer, ovarian cancer, prostate cancer, breast cancer, or lung cancer.

19. The method according to claim 16, wherein said cancer is in the form of a liquid tumor.

20. The method according to claim 19, wherein said cancer is lymphocytic leukemia, Hodgkin's disease, non-Hodgkin's lymphoma, multiple myeloma, or acute lymphocytic leukemia.

* * * * *